United States Patent
Chen et al.

(10) Patent No.: US 6,689,161 B2
(45) Date of Patent: Feb. 10, 2004

(54) DECELLULARIZED VASCULAR PROSTHESES RESISTANT TO THROMBUS OCCLUSION AND IMMUNOLOGIC REJECTION

(75) Inventors: Changyi Chen, Decatur, GA (US); Alan B. Lumsden, Atlanta, GA (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/844,961

(22) Filed: Apr. 27, 2001

(65) Prior Publication Data

US 2001/0044654 A1 Nov. 22, 2001

Related U.S. Application Data

(60) Provisional application No. 60/200,220, filed on Apr. 28, 2000.

(51) Int. Cl.$^7$ .................................................. A61F 3/06
(52) U.S. Cl. ...................... 623/1.43; 623/23.72; 606/36
(58) Field of Search ................................ 623/1.1, 1.13, 623/1.24–1.26, 1.38, 1.42–1.44, 1.46–1.48, 2.1, 2.13, 2.15–2.16, 11.11, 12, 915–917, 921, 23.64, 23.68, 23.7, 23.72–23.76; 427/2.24; 424/422–423; 600/36; 606/191–192, 194–195, 198

(56) References Cited

U.S. PATENT DOCUMENTS

| | | | |
|---|---|---|---|
| 4,034,750 A | | 7/1977 | Seiderman |
| 4,795,741 A | | 1/1989 | Leshchiner et al. |
| 4,798,606 A | | 1/1989 | Pinchuk |
| 5,336,616 A | | 8/1994 | Levesey et al. |
| 5,475,052 A | | 12/1995 | Rhee et al. |
| 5,516,533 A | | 5/1996 | Badylak et al. |
| 5,613,982 A | | 3/1997 | Goldstein |
| 5,632,778 A | * | 5/1997 | Goldstein ................... 128/898 |
| 5,899,936 A | | 5/1999 | Goldstein |
| 5,910,170 A | * | 6/1999 | Reimink et al. ............ 623/2.38 |
| 6,387,116 B1 | * | 5/2002 | McKenzie et al. ............. 604/22 |
| 2002/0077697 A1 | * | 6/2002 | Ranieri et al. ............. 623/1.41 |

FOREIGN PATENT DOCUMENTS

| | | |
|---|---|---|
| WO | WO95/29712 | 4/1994 |
| WO | WO 98/04300 | 2/1998 |
| WO | WO 98/46165 | 10/1998 |
| WO | WO 98/50082 | 11/1998 |
| WO | WO 00/43050 | 7/2000 |

OTHER PUBLICATIONS

MacIntosh, F.C., A Colorimetric Method For The Standardization of Heparin Preparations. Biochem J 1941; 35:776–782.

Smith, P.K., Mallia, A.K., Hermanson, G.T., Colorimetric Method For Assay of Heparin Content in Immobilized Heparin Preparation. Analytical Biochem 1990; 109:466–473.

Charriere, G., Bejot, M., Schnitzler, L., Ville, G., Hartmann, D.J., Reactions To A Bovine Collagen Implant. Clinical and Immunologic Study in 705 Patients. J Am Dermatol 1989; 21:1203–1208.

(List continued on next page.)

*Primary Examiner*—David J. Isabella
*Assistant Examiner*—Urmi Chattopadhyay
(74) *Attorney, Agent, or Firm*—Fulbright & Jaworski L.L.P.

(57) ABSTRACT

Decellularized vascular prostheses that are resistant to thrombus occlusion and have a low level of immunogenicity and methods of making same are disclosed. The prostheses have high mechanical strength, resist aneurysm, rupture, and allow for secure surgical sutures while maintaining structural integrity. The vascular prostheses provided are blood vessels, valves or portions of vessels containing valves. There is also a method useful for coating synthetic vascular stents.

15 Claims, 9 Drawing Sheets

OTHER PUBLICATIONS

The Canadian Multicenter Hemashield Study Group: Immunologic response to collagen–impregnated vascular grafts: A randomized prospective study. J Vasc Surg. 1990; 12:741–746.

Chen, C., Hughes, J.D., Mattar, S.G., Hanson, S.R., Lumsden, A.B. Transgraft Infusion Of Heparin To Prevent Early Thrombosis Of Expanded Ptfe Grafts In Canine Femoral Veins. Ann Vasc Surg 1996; 10:147–155.

Moscatelli, D. High and Low Affinity Binding Sites For Basic Fibroblast Growth Factor On Cultured Cells: Absence Of A Role For Low Affinity Binding In The Stimulation Of Plasminogen Activator Production By Bovine Capillary Endothelial Cells. J Cell Physiol 1987; 131:123–130.

Chard, R.B., Johnson, D.C., Nunn, G.R., Cartmill, T.B. Aorta–Coronary Bypass Grafting With Polytetrafluoroethylene Conduits. Early And Late Outcome In Eight Patients. J Throrac Cardiovasc Surg 1987; 94: 132–134.

Dardik, H., Miller, N., Dardik, A., Ibrahim, I.M., Sussman, B., Berry S.M., Wologiger, F., Kahn, M., And Dardik, I. A Decade of Experience With The Glutaraldehyde–tanned Human Umbilical Cord Vein Graft For Revascularization of the Lower Limb. J Vasc Surg. 1988; 7:336–346.

Vrandecic, M.O.P., MD, New Graft For The Surgical Treatment of Small Vessel Diseases. J Cardiovasc Surg 1987; 28:711–714.

Lumsden, A.B., Kelly, A.B., Schneider, P.A., Krupski, W.C., Dodson, T., Hanson, S.R., Harker, L.A. Lasting Safe Interruption of Endarterectomy Thrombosis By Transiently Infused Antighrombin Peptide D–Pro–ArgCh2Cl in Baboons. Blood 1993' 81:1762–1770.

Chen, C., Hanson, S.R., Lumsden, A.B. Boundary Layer Infusion of Heparin Prevents Thrombosis and Reduces Neointimal Hyperplasia In Venous PTFE Grafts Without Systemic Anticoagulation. J Vas Surg 1995; 22:237–47.

Chen, C., Mattar, S.G., Hughes, J.D., Hanson, S.R., KU D.N., Lumsden, A.B. Recombinant Mitotoxin Basic FGF–Saporin Reduces Venous Intimal Hyperplasia. *Circulation* 1996; in press.

Veith, F.J., Gupta, S.K., Ascer, E., White–Flores, S., Samson, R.H., Scher, L.A., Towne, J.B., Bernhard V.M., Bonier, P., Flinn, W.R., Astelford, P., Yao, J.S.T., And Bergan, J.J. Six Year Prospective Multicenter Randomized Comparison of Autologous Saphenous Vein and Expanded Polyterafluoroethylene Grafts In Infrainguinal Arterial Reconstructions. J Vasc Surg. 1986; 3:104–114.

Whittermore, A.D., Kent, K.C., Donaldson, M.C., Couch, N.P., and Mannick, J.A., What Is The Proper Role of Polytetrafluoroethylene Grafts in Infrainguinal Reconstruction? J Vasc Surg. 1989; 10:299–305.

Mitchell, I.M., Essop, A.R., Scott, P.J., Martin, P.G., Gupta, N.K., Saunders, N.R., Nair, R.U., Williams, G.J. Bovine Internal Mammary Artery As A Conduit For Coronary Revascularization: Long–Term Results. Ann Thorac Surg 1993; 55:120–122.

Browse, N.L. The Course of Venous Ulceration. Lancet 1982; 2:243–245.

Kistner, Robert L. Surgical Repair of the Incompetent Femoral Vein Valve. Arch Surg 1975 110:1336–1342.

Esquivel, C.O., Bjorck, C.G., Bergqvist, D., Rothman, V., Bergentz, S.E. Decreased Acute Thrombogenicity of Human Umbilical Veins After Heparin and Alcohol Treatment. Eur Surg Res 1983; 15:123–128.

Esquivel, C.O., Bjorck, C.G., Bergqvist, D., Bergentz, S.E. Heparinized Human Umbilical Vein Grafts. Delayed Heparin Desorption After Alcohol Treatment. Eur Surg Res 1983; 15:289–296.

Klagsbrun, M., Shing, Y. Heparin Affinity of Anionic and Cationic Capillary Endothelial Cell Growth Factors: Analysis of Hypothalamus–Derived Growth Factors and Fibroblast Growth Factors. Proc Natl Acad Sci USA, 1985; 82:805–809.

Sevitt, S. The Mechanisms of Canalization In Deep Vein Thrombosis. J Pathol 1973; 110:153–65.

Kistner, R.L. Primary Venous Valve Incompetence of the Leg. Am J Surg 1980; 140:218–224.

Oliver, R.F., Hulme, M.J., Mudule, A., Grant, R.A. Skin Collagen Allografts In The Rat. Nature 1975; 258:537–539.

Cooke, A., Oliver, R.F., Edward, M. An In Vitro Cytotoxicity Study of Aldehyde–Treated Pig Dermal Collagen. Br J Exp Pathol 1983; 64:172–176.

Silver, G.M., Katske, G.F., Stutzman, F.L., Wood, N.E. Umbilical Vein For Aortocoronary Bypass. Angiology 1982; 33:450–453.

Dale, W.A., And Lewis, M.B. Further Experiences With Bovine Arterial Grafts. Surgery 1976; 80:711–721.

Rosenberg, N., Thompson, J.E., Keshishian, J.M., and Vanderwerf, B.A. The Modified Bovine Arterial Grafts. Arch Surg. 1976; 111:222–226.

Wesolowski, S.A., Fries, C.C., Henningar, G., Fox, I.M., Sawyer, P.N., Sauvage, I.R. Factors Contributing To Long Term Failures In Human Vascular Prosthetic Grafts. J Cardiovasc Surg 1964; 5:544–567.

Piccone, Vincent A. Alternative Techniques In Coronary Artery Reconstruction. In: Modern Vascular Grafts. Sawyer PN (ed), McGraw–Hill Book Company, New York, 1987; pp. 253–260.

Berger, Knute, Sauvage, I.R., Rao, A.M., Wood, S.J. Healing of Arterial Prostheses In Man: its incompleteness. Ann Surg 1972; 175:118–128.

Yaw, P.B., Grisell, T.W., Wahle, W.M., Schmacker, H.B., Glover, J.L. Fate of a Nylon Vascular Prosthesis For Aortic Replacement: 14 year follow–up study. Surgery 1974; 75:140–144.

Debakey, M.E., Jordan, G.L., Abbott, J.P., O'Neal, R.M., Halpert, B. The Fate of the Dacron Vascular Grafts. Arch Surg 1964; 80:754–782.

Szilagi, D.E., Smith, R.F., Elliott, J.P., Allen, H.M. Long Term Behavior of a Dacron Arterial Substitute. Ann Surg 1965; 162:453–477.

Bayer, E.A., Wilchek, M. The Use of the Avidin–Biotin Complex As A Tool In Molecular Biology. Methods Biochem Annal. 1980; 26:1–45.

Wilson, N.M., Rutt, D.L., Browse, N.L. Repair and Replacement of Deep Vein Valves in the Treatment of Venous Insufficiency. Br J Surg 1991; 78:388–394.

Criado, E., Johnson, G. Venous Disease: Anatomic and Functional Considerations. Curr Probl Surg 1991; 338–400.

Senatore, F., Shankar, H., Chen, J.H., Avantsa, S. In Vitro and In Vivo Studies of Heparinized–Collageno–Elastic Tubes. J Biomed Mat Res 1990; 24:939–957.

Bashkin, P., Doctrow, S., Klagsbrun, M., Svahn, C.M., Folkman, J., Vlodavsky, I. Basic Fibroblast Growth Factor Binds to Subendothelial Extracellular Matrix and Is Released By Heparitinase and Heparin–like Molecules, Biochemistry 1989; 28:1737–1743.

Boerboom, L.E., Olinger, G.N., Karas, B.J., Lindon, J.N., Rosen, L.Z., Thyagarajan, K., Tu, R. Heparinization of Biological Vascular Graft Reduces Fibrin Deposition. Int J Artif Organs 1993; 16:263–267.

Suma, H., Wanibuchi, Y., Terada, Y., Fukuda, S., Saito, T., Isshiki, T., Yamaquchi, T. Bovine Internal Thoracic Artery Graft. Successful Use At Urgent Coronary Bypass Surgery. J. Cardiovasc Surg 1991; 32:268–270.

Raju, S., Fredericks, R. Valve Reconstruction Procedures For Nonobstructive Venous Insufficiency: Rationale, Techniques, and Results in 107 Procedures With Two-to-Eight-Year Follow-Up. J Vasc Surg 1988; 7:301.

Rosenberg, M.B., Hawrot, E., Breakefield, X.O. Receptor Binding Activities of Biotinylated Derivatives of ss-nerve Growth Factor. J Neurochem 1986; 46:641–648.

Pieper, J.S. et al., "Development of tailor-made collagen-glycosaminoglycan matrices: EDC/NHS crosslinking, and ultrastructural aspects," Biomaterials, pp. 581–593 (2000).

Chen, Changyi, M.D. et al., "Tenascin: A Potential Role in Human Arteriovenous PTFE Graft Failure", Journal of Surgical Research, vol. 60, pp. 409–416 (1996).

Martin, Franklin H., M.D., "The Effect of Thrombophlebitis On The Venous Valve", The Surgical Publishing Company of Chicago, vol. 65, pp. 310–320 (Jul.–Dec. 1937).

Sauvage, Lester R. et al., "Composite Biosynthetic Prostheses of Fibrin and Filamentous Knitted Dacron for Abdominal and Lower Extremity Arterial Surgery", Grune & Stratton, Inc., a subsidiary of Harcourt Brace Jovanovich Publishers, pp. 533–552 (1982).

Guidoin, Robert Ph.D. et al., "Pathologic Features of Surgically Excised Human Umbilical Vein Grafts", J Vasc Surg., 3:146–54 (1986).

* cited by examiner ced # DECELLULARIZED VASCULAR PROSTHESES RESISTANT TO THROMBUS OCCLUSION AND IMMUNOLOGIC REJECTION

CROSS REFERENCE TO RELATED APPLICATIONS

This application claims priority from U.S. Provisional Application No. 60/200,220 filed on Apr. 28, 2000.

TECHNICAL FIELD

The present invention relates to decellularized vascular prostheses that are resistant to thrombus occlusion and have a low level of immunogenicity. The vascular prostheses are denuded of cells, and coated with an anti-thrombogenic agent and a growth factor that promotes recellularization and further reduces the immunogenicity.

BACKGROUND OF THE INVENTION

Chronic venous insufficiency is a major health problem in the United States and throughout the world. More than 7 million people are afflicted and at least 500,000 develop leg ulcerations as a consequence. An estimated 900,000 new cases arise annually. Chronic venous insufficiency is a general term that encompasses all causes of chronic venous disease. It occurs in a primary form with stretched valves and dilated venous walls, and in a secondary form following thrombophlebitis, with scarred and deformed valves and thickened venous walls with longitudinal septa and seriously compromised lumens. Other causes of venous insufficiency, such as valve aplasia, congenital malformations and external obstruction occur less often.

The clinical symptoms associated with venous insufficiency range from severe pain and recurrent ulcerations to no manifest symptoms. The site of involvement appears to be critical to the severity of the symptoms. Thus, varicosity of the superficial venous system is usually benign and the incidence of significant complications is low. In contrast, insufficiency of the deep veins or of the perforating vessels is more frequently associated with pain, swelling, ulceration, and long-term disability.

The current basic treatments for venous insufficiency rely on the prevention of reflux and a reduction of venous pressure. Conservative treatments, however, including bed rest, limb elevation, mild diuretic administration, and elastic compression stockings are aimed at the relief of symptoms rather than the underlying disease process. They are not particularly successful.

Direct valvuloplasty may be accomplished by tightening redundant cusp edges, whereas indirect valvuloplasty employs a DACRON or polytetrafluoroethylene (PTFE) cuff around the valve. Despite noticeable gains in hemodynamic measurements, clinical improvement is frequently less evident. Venous valve repair and replacement are attempts to restore competence to the deep venous system. Venous valve repair, however, suffers from the limitation that it is only suitable for those patients without prior deep venous thrombosis. In the event that the valve apparatus has been significantly degraded or destroyed, valve transplantation may be the only available option to offer symptomatic relief and a fall in venous pressure.

The quantity and quality of donor valves remain significant problems. In the typical patient as many as 30% to 40% of brachial or axillary valves are incompetent. Additionally, many patients have dilated venous systems that will not accommodate a smaller-caliber brachial or axillary vein graft. Accordingly, valve transplantation suffers from considerable constraints in its use as a surgical technique.

Small caliber vascular grafts with inner diameters of less than 6 mm are used extensively in aorta-coronary artery and infrapopliteal artery bypasses for the treatment of arterial occlusive diseases, and as arterio-venous conduits for hemodialysis access in the end stage of renal disease. At present, autogenous saphenous veins continue to be the most widely used vascular prostheses for small caliber arterial reconstructive procedures. Primary patency at four years for an arterial bypass with saphenous veins is 40–70%. A practical impediment to constructing such bypasses, however, is the fact that 10 to 40% of patients do not have an acceptable saphenous vein that can be transplanted for a successful graft.

Previous harvesting of vascular tissue for use in cardiac or vascular surgical procedures, varicose vein stripping, and prior thrombophlebitis are the most common reasons for unsuccessful autogenous saphenous vein grafting. Alternative sources of small-caliber vascular prostheses, with a patency rate comparable to or better than that of the autogenous saphenous vein, are urgently needed for clinical use.

Venous allografts from cadavers have also been used. They provide reasonable function early in the life of the graft, but yield poor results after 2 years. Modern cryopreservation techniques, including controlled-rate freezing, storage at −190° C., and cryoprotectants such as dimethyl sulfoxide and chondroitin sulfate, improve the viability of cryopreserved allograft saphenous veins. Successful results using unmodified cryopreserved allograft saphenous veins for infrainguinal tibial artery reconstructions have achieved a one-year patency rate in the range of 10 to 50%. Long-term benefits to the patient have been marred, however, by vein graft rejection and unheralded early graft closure. Complications related to the mechanical failure of the conduit itself, such as graft aneurysms or ruptures, have occurred with greater frequency and caused greater morbidity, compared to fresh autogenous veins.

Synthetic DACRON and PTFE vascular prostheses have achieved some degree of clinical success even though they are not ideal in large and mid-sized arterial reconstructions. In addition, vessel substitutes smaller than 6 mm in diameter are susceptible to early graft occlusion. The most frequently encountered failures of synthetic grafts result from thrombosis and anastomotic hyperplasia. The inherent properties of synthetic graft materials, and their limited spontaneous re-endothelialization in humans, contribute to high surface thrombogenicity.

The implantation of glutaraldehyde-fixed bovine and human umbilical vein grafts was extensively evaluated and largely discarded because of high rates of aneurysm formation occurring two years after implantation. Most of these grafts failed because of delayed vascular healing and degenerative changes. An immune response to the highly immunogenic, chemically modified venous material, was characterized by invasion of multinucleated giant cells and reduced implant recellularization. Furthermore, glutaraldehyde fixation disturbed the natural matrix protein configuration. The cytotoxic effect of glutaraldehyde inhibited cell migration into the graft wall. Degeneration in the grafts resulted in a highly thrombogenic surface and the consequent occlusion of the vessels by thrombosis.

Many factors contribute to the degree of patency achieved with a particular prosthesis. These include the inherent properties of the chosen materials, surface thrombogenicity, compliance, and porosity in the case of textile grafts. The surface properties of materials seem to be a key issue in securing the desired long-term patency of small vessel substitutes. Numerous researchers have attempted to optimize the clinical efficacy of small diameter vascular grafts by modifying the prosthetic materials to make them biologically inert, but such an inert material has yet to be developed. An alternative approach to optimize the biological components of the prosthesis-tissue complex has led to the development of biohybrid materials. Some examples include synthetic material seeded with viable cells, coatings of biological compounds such as albumin and collagen, and materials synthesized from polymers known to elicit favorable biological responses. This approach has also not yielded a practical or effective vascular prosthesis.

In general, biological materials obtained from animals or humans have unique and special microstructural, mechanical, hemodynamical, and biochemical properties that cannot be completely replicated by currently available technology. Therefore, biologically-derived materials have great potential as raw materials for implantable artificial organs. The use of porcine organs for xenotransplantation is an attractive option to overcome the shortage of available organs for transplantation into humans. However, the problem of acute rejection remains an unsolved barrier. Cell surface molecules of xenogenic organs are mainly responsible for eliciting host rejection responses. Thus, immune rejection of allogenic or xenogenic tissues and the resulting decrease in long-term durability of the graft are major obstacles to the successful development of the ideal graft.

The most immunogenic portions of allogenic or xenogenic vascular grafts are the cellular components. Mature collagen, in contrast, shows low or no antigenicity, especially when transferred from individuals of the same species. For example, induction of an immunological response against purified bovine collagen is extremely low when injected for cosmetic purposes, or in vascular grafts impregnated with bovine collagen. Chemical cross-linking of collagen, on the other hand, renders the collagen highly immunogenic and can drastically reduce its biocompatibility with the host.

A readily available, synthetic, biologic or biohybrid venous valve in various sizes would greatly facilitate valve reconstruction surgery, including the desirable goal of valve insertions in multiple sites. The development of a vascular vessel or venous valve prosthesis that avoids the long-term likelihood of thrombosis and immune rejection would revolutionize the treatment of chronic venous insufficiency.

Problems of thrombogenicity and poor tissue compatability are also encountered with implantable vascular stents. Vascular stents are supporting devices, used to strengthen or dilate a blood vessel after balloon angioplasty or endarterectomy. They are made of synthetic material that is typically thrombogenic and has poor tissue compatibility. Stents fail primarily due to thrombotic occlusion and restenosis from tissue overgrowth.

What is needed, therefore, is a graft that is durable and can maintain structural integrity. Specifically, it must retain mechanical strength in all dimensions so that dilational and elongation distortions are minimized. The graft must be capable of long-term storage. It must be available in many sizes to accommodate the wide variation of vascular reconstructions. The prosthesis must resist infection. Intraoperatively, the ideal graft should have excellent handling characteristics, including flexibility, ease of suture placement, and minimal needle-hole and interstitial bleeding. The compliance of the ideal graft should closely approximate that of the host vessel. Ideally, turbulence about the anastomoses should be minimized to decrease intimal hyperplasia. In addition, the luminal surface should be resistant to platelet aggregation and thrombosis following placement in the patient, and avoid the immunogenicity that can arise from chemical modification of biological material. Finally, in this era of cost-containment, the graft must be relatively inexpensive and easy to manufacture.

SUMMARY OF INVENTION

The present invention solves the problems described above by providing decellularized vascular prostheses covalently linked with at least one anti-thrombogenic agent and at least one growth factor. The decellularized blood vessels and vascular valves comprise collagen and elastin matrix proteins of minimal immunogenicity, an anti-thrombogenic agent and a growth factor to promote recellularization of the graft.

The vascular prostheses that are the subject matter of the present application have novel properties that offer advantages over current synthetic or unmodified natural vascular grafts. Decellularization of the grafts eliminates the major factor inducing immunological rejection. These prostheses are also suitable substrates for host vascular cell invasion, cell attachment, proliferation, migration, and differentiation, since they consist of native matrix proteins.

Covalent linkage of the vascular prostheses with an anti-thrombogenic agent, including but not limited to heparin, offers a non-covalent attachment site for growth factors such as heparin-binding growth factors including, but not limited to, basic fibroblast growth factor (bFGF) that will improve and accelerate vascular healing and the remodeling process. Thus, the bioengineered biological vascular prostheses of the present invention have long term patency and less likelihood of post-operative complications. These grafts benefit patients by increasing the rate of recovery and decreasing the possibility of rejection or blockage of the graft.

The decellularized grafts of the present invention consist primarily of collagen and elastin matrix proteins, which are highly conserved among species and have low immunogenicity. This permits the use of xenogenic grafts from one species to another, reduces the current reliance upon allogenic sources of transplant material, and significantly expands the supply of available prostheses. The decellularized matrix is stable during long-term storage so that a graft of choice will be readily available when needed. This property allows the vascular surgeon to select a prosthesis that more closely matches the diameter of the recipient blood vessel. An improved blood flow is thereby obtained that is less likely to result in anastomotic thrombus formation.

The vascular prostheses of the present invention also permit other pharmaceutically active agents to be bound or otherwise immobilized to the immunologically inert biological matrix. This, and other advantages of the present invention, cannot be achieved by currently available technologies.

Accordingly, it is an object of the present invention to provide a vascular prosthesis that may include an anti-thrombogenic agent immobilized to the decellularized vascular prosthesis to create surfaces with reduced thrombogenicity.

It is another object of the present invention to provide a vascular prosthesis with reduced immunogenicity that retains a high degree of mechanical strength for long-term durability and suitability for surgical implantation.

It is yet another object of the present invention to provide a vascular prosthesis that is stable during storage.

Yet another object of the present invention is to provide a decellularized vascular prosthesis that retains sufficient mechanical strength to resist aneurysm formation, and supports surgical stitching with minimal leakage at the point of suture.

Another object of the present invention is to combine decellularized, anti-thrombogenic, growth factor-bound vascular prostheses with synthetic vascular stents and stent-valve devices.

Still another object of the present invention is to provide a method to decellularize vascular tissue so that it has reduced thrombogenicity and immunogenicity and approximates the mechanical strength of the native blood vessel.

It is also an object of the present invention to provide a method of linking decellularized vascular tissue with at least one anti-thrombogenic agent and applying a second linking of at least one cellular growth factor so that the modified vascular tissue may be used as a vascular prosthesis.

The decellularized, heparinized, and growth factor-bound vascular tissues of the present invention are superior to currently used prostheses since they provide xenogenic grafts with reduced propensity towards immunological rejection.

Still another advantage of the present invention is that the decellularized, heparinized, growth factor-bound vascular prostheses have application in multiple vascular replacement or reconstruction procedures, venous valve transplantations for chronic venous insufficiency, vein replacement, heart valve replacement, and as a vascular patch after carotid artery endarterectomy, femoral artery thrombectomy, and other vascular wall repairs.

A further advantage of the present invention is that the combination of a decellularized vascular implant, heparin, and the heparin-binding growth factor provides a new platform technology for development of many medical products.

These and other features, objects and advantages of the invention and preferred embodiments of the present invention will become apparent from the detailed description that follows.

DETAILED DESCRIPTION OF THE INVENTION

Figure 1A:
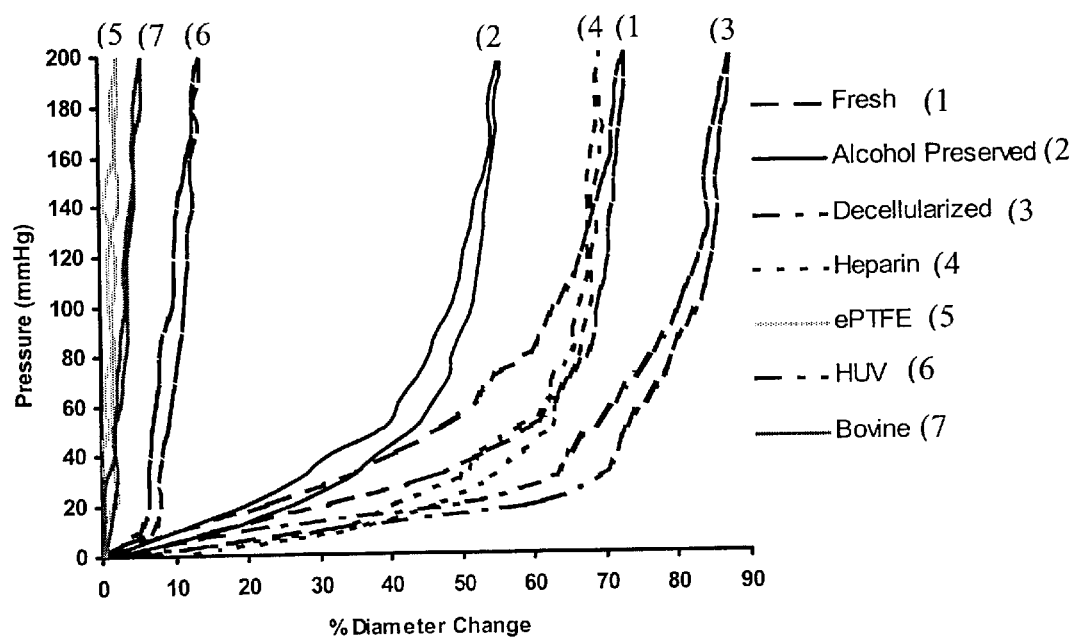
FIGS. 1A and 1B show the compliance (elasticity) of different vascular prostheses as shown by changes in the diameters of the prostheses at various intraluminal pressures.

In one embodiment, the present invention provides decellularized vascular prostheses that have an anti-thrombogenic agent immobilized thereon and a growth factor bound to the anti-thrombogenic agent. Removal of the cellular component of the vascular tissue eliminates the major source of antigenic determinants of the tissue, and greatly reduces the immunogenic potential of the grafts. The anti-thrombogenic agent reduces the likelihood of vascular thrombosis that typically causes post-operative complications because of the highly thrombogenic nature of the newly exposed collagen of the denuded graft.

Coating the graft tissue with at least one growth factor promotes recellularization of the inert matrix tissue, which significantly increases the patency of the graft, and diminishes the possibility of rejection or stenosis of the vessel. This lessens discomfort and risk to the patient who would otherwise need further corrective measures, including additional surgery. In one embodiment the present invention offers an immunologically inert, prosthetic material that is stable during long-term storage, may be readily coated with growth factors and improves the prognosis for a successful vascular graft. These grafts are immunologically acceptable to the recipient, and resist thrombotic or restenotic occlusion.

In another embodiment, the present invention provides methods to decellularize a dissected vascular tissue and link the extracellular matrix with an anti-thrombogenic agent and a growth factor. This method employs sequential steps of soaking the tissue in water, mechanically removing cellular debris, and then treating the tissue with at least one protease, at least one lipase, and at least one nuclease. The prosthesis is rinsed in at least one detergent and stored by any means known to one of ordinary skill in the art so that its structural and mechanical integrity, and the anti-thrombogenic coating are maintained.

The term "vascular tissue" is used herein to mean a blood vessel, a portion thereof, one or more valves dissected from a blood vessel, a valve retained within a portion of a blood vessel, an aortic or pulmonary valve dissected and free of non-valvular tissue, an aortic or pulmonary valve retained within a dissected blood vessel or cardiac tissue, or any other vascular tissue that may be suitable for use as a prosthesis. Blood vessels may include arteries and veins, portions thereof, and vascular beds containing arteries or veins.

The term "decellularized" is used herein to mean that physical, chemical, or enzymatic means, or any combination thereof, has removed the cellular component of vascular tissue thereof. The remaining decellularized vascular tissue comprises the extracellular matrix of the native vascular tissue and may include, but is not limited to, elastin, collagen, fibrin, and other extracellular proteins or non-proteinaceous compounds found in vascular tissue, or any combination thereof known to one of ordinary skill in the art.

The terms "prosthesis", "vascular prosthesis", "vascular prostheses" or "vascular implant" are used herein to mean a surgical implant or implants derived from, or inserted into, the vascular system of a human or animal patient. The term is intended to apply to surgical implants made of synthetic or natural materials or any combination thereof including, but not limited to, decellularized vascular tissue.

The term "graft" is used herein to mean any surgical implant, either derived from the tissues of the recipient patient, or from the tissues of a donor of the same or different species as the recipient. The graft may be fully or partially synthetic, and comprised of any suitable material well known to one of ordinary skill in the art.

The term "anti-thrombogenic agent" is used herein to mean any compound, or combination of compounds, that minimize the induction of thrombus formation, or the stability of the thrombus. Anti-thrombogenic compounds include glycosaminoglycans such as heparin, heparin sulfate, dermatan sulfate and any other glycosaminoglycan with anti-thrombotic activity known to one skilled in the art. Anti-thrombogenic compounds may also include dextran and derivatives thereof, hirudin and derivatives thereof, and coumarin and derivatives thereof, including but not limited to 4-hydroxycoumarin, warfarin, dicumarol, phenprocoumon and acenocoumarol, indan-1,3-dione, anisindone, and any other related compounds known to one skilled in the art. The anti-thrombogenic compound may include thrombolytic agents including, but not limited to, proteins that dissolve blood thrombi, including urokinase, plasminogen activator, antithrombin III, and modified forms thereof. The anti-thrombogenic compound may also include any other compound that may be immobilized on a decellularized vascular prosthesis and which inhibits the formation of, or participates in the destabilization of, thrombotic occlusions of the vascular prosthesis.

The term "growth factor" is used herein to mean any protein or non-proteinaceous compound capable of inducing or promoting the growth of cells. Such cells include, but are not limited to, endothelial cells, smooth muscle cells and fibroblasts. Growth factors may include, but are not limited to, fibroblast growth factor (FGF), basic fibroblast growth factor (bFGF), acidic fibroblast growth factor (aFGF), heparin-binding epidermal growth factor (HBEGF), platelet-derived growth factor (PDGF), epidermal growth factor (EGF), transforming growth factor alpha (TGF-α), transforming growth factor beta (TGF-β), vascular endothelial cell growth factor (VEGF), placenta growth factor (PlGF), insulin-like growth factor (IGF), or any other growth factor, fragment or derivative thereof known to one skilled in the art.

The terms "stent" and "vascular stent" are used herein to mean a prosthetic device implanted in a patient, either within the lumen of a blood vessel, or enveloping the exterior of a blood vessel. The device may be comprised in whole or in part of a synthetic material including, but not limited to, DACRON, PTFE or any other material used by one of ordinary skill in the art. The synthetic stent device may also be combined with biologically-derived material, or comprised solely of non-synthetic material.

The term "allogenic" is used herein to mean a graft or transplant of surgically implanted material obtained from a donor of one species and used in a recipient of the same species.

The term "xenogenic" is used herein to mean a graft of surgically implanted material donated by an animal of one species and implanted into a recipient animal of another species. Donor species may include, but are not limited to pigs, sheep, cows, various primate species, humans, and any genetically modified variants thereof.

The terms "protease" or "peptidase" are used herein to mean any enzyme which is capable of digesting a protein to peptides, or a peptide to its constituent amino acids including, but not limited to, trypsin, proteinase K, or any other protease or peptidase that is known to one of ordinary skill in the art.

The term "lipase" is used herein to mean any enzyme, modified enzyme or combinations thereof, capable of digesting lipids, that is known to one of ordinary skill in the art.

The term "nuclease" is used herein to mean an enzyme or chemical procedure or combination thereof, that will specifically degrade and destroy nucleic acids including, but not limited to, deoxyribonuclease (DNAse), ribonuclease (RNAse), micrococcal nuclease, exonuclease III, S1 nuclease, or any other nuclease known to one of ordinary skill in the art.

The term "detergent" is used herein to mean any compound, or composition that is capable of solubilizing and extracting lipids from tissue including, but not limited to, Triton X-100, sodium dodecyl sulfate (SDS), sodium lauryl sulfate (SLS), or any other detergent or combination thereof known to one of ordinary skill in the art.

Removal of the cellular component of vascular tissue eliminates the principal source of the immunogenicity of a vascular prosthesis obtained from a natural donor. The present invention does not introduce artificial immunogenicity since chemical cross-linking of the matrix proteins is avoided.

The prostheses of the present invention have several uses including, but not limited to, arterial reconstruction procedures, treatment of obstructive arterial diseases, venous replacement or reconstruction procedures, treatment of obstructive venous diseases, venous valve transplants, and modification of vascular stents for use in the treatment of vascular stenotic diseases. The present invention is suitable as a prosthetic replacement for, but not limited to, small caliber vessels in aorta-coronary artery, external iliac artery and infrapopliteal artery bypasses, the superior and inferior vena cava and portal vein, and the external iliac and other veins of the limbs, deficiencies in which cause chronic venous insufficiency. A stent-valve device can also be used for a minimally invasive approach to venous valve transplantation. A vascular patch can be used for carotid artery endarterectomy, femoral artery thrombectomy, and vascular wall repairs.

Heparin exerts a powerful anticoagulant effect by inducing the inhibitory action of antithrombin III. Several growth factors involved in vascular healing have a high affinity for binding to heparin. bFGF is a heparin-binding growth factor with potent effects on endothelial cell and smooth muscle cell proliferation and migration. When successfully bound to a heparinized surface, bFGF promotes host cell proliferation and migration into the graft, accelerating vascular healing and remodeling, reducing graft degeneration.

A stent device may further support the heparinized and growth factor-coated decellularized vascular prosthesis. The stent may be placed adjacent to the outer surface of the vascular vessel, or inserted into the lumen of the graft so that its outer surface is adjacent to the interior surface of the vessel. This approach provides mechanical support to the denuded vessel until such time as recellularization has strengthened the matrix by a fresh deposition of collagen, elastin and other matrix components. The stent will counteract any tendency towards rupture of the implanted prosthesis.

A prosthetic vascular valve that is decellularized and coated with an anti-thrombogenic agent and a growth factor in accordance with the present invention, is fully functional and represents a major advance over alternative means to remediate venal insufficiency, such as venous cuffs, application of exterior pressure to an affected limb, and administration of diuretics.

The present combination of decellularization, heparin linkage, and a heparin-binding growth factor is a new platform technology for the development of many medical products. It also offers a means to attach additional pharmaceutically active agents to the immunologically inert biological matrix.

After implantation of a bioengineered vascular xenograft of the present invention into humans or other species of animals, host cells rapidly repopulate the acellular xenograft. Under proper hemodynamic stimulation and matrix protein remodeling, host vascular smooth muscle cells and endothelial cells invade the prosthesis and become established in the media and on the luminal surface, respectively, of the graft. Eventually, the xenograft is similar to a native vascular structure with functional cell types and matrix components, and provides extended patency.

In one embodiment of the present invention, an anti-thrombogenic agent is immobilized to and coats a decellularized vascular tissue, thereby rendering it less thrombogenic. The coated prosthesis also includes an immobilized growth factor that retains its physiological function and interacts with endothelial cells, smooth muscle cells, or fibroblasts, so as to promote recellularization following implantation of the vascular prosthesis.

In a preferred embodiment of the present invention, the anti-thrombogenic agent is heparin. The growth factor may be any factor that will accelerate vascular graft healing and the remodeling process, significantly improving the long-term patency of the bioengineered biological grafts. The preferred growth factor may be, but is not limited to, a heparin-binding growth factor such as bFGF or aFGF that has high affinity for the heparin bound to the decellularized vascular grafts.

In a more preferred embodiment, heparin is covalently bound to the surfaces of the decellularized vascular tissue by means of a linker molecule such as, but not limited to, 1-ethyl-3[3-dimethylaminopropyl]carbodiimide. The preferred heparin-binding growth factor is bFGF, which is bound to the heparin on the surfaces of the vascular tissue.

In one embodiment of the present invention, the decellularized vascular tissue is an arterial vascular graft, which may be allogenic or xenogenic with respect to the recipient of the graft.

In yet another embodiment, the vascular tissue is a venous vascular graft, which may be allogenic or xenogenic with respect to the recipient of the graft.

In a further embodiment, the vascular tissue is a venous valve prosthesis, wherein the dissected vein segment contains at least one functional valve that can be decellularized, heparinized, and have growth factors immobilized thereon without loss of valve function.

Yet a further embodiment of the present invention provides a vascular stent cover, wherein allogenic or xenogenic veins or arteries can be decellularized, heparinized, and growth factors bound to heparin according to the present invention. The vascular prostheses can be applied to either the interior or the exterior surfaces of vascular stents, before or after surgical implantation into the host. The stents can be of any suitable material known to one skilled in the art. Vascular stents or stent-valve devices can be applied to venous valve prostheses of the present invention for a minimally invasive approach to venous valve transplantation.

Yet another embodiment of the present invention is a vascular patch, wherein allogenic or xenogenic veins or arteries can be decellularized, heparinized, treated with growth factors and used as arterial and venal patch materials in procedures such as carotid artery endarterectomy and femoral artery thrombectomy, vein replacement and vein injury repair.

Another embodiment of the present invention is a method to decellularize vascular tissue, link the tissue with at least one anti-thrombogenic agent and apply a second coating of at least one growth factor.

In one preferred embodiment of the present invention the dissected vascular tissue is decellularized by sequentially washing the tissue with hypotonic solution and mechanically removing cellular debris. Mechanical removal methods may include, but are not limited to, scrapping, shaking, removal by forceps or other suitable instrument, cutting or by any other method well known to one of ordinary skill in the art. The partially decellularized prosthesis may then be treated with at least one protease, at least one lipase, at least one nuclease and at least one detergent, so that the extracellular matrix of the prosthesis is denuded of cellular material.

The protease may be in the concentration range of at about 0.1% w/v to approximately 10% w/v. The period of treatment with the protease may be from at least 5 min to approximately one hour, and at a temperature from at about 20° C. to approximately 37° C.

The lipase may be in the concentration range of at about 0.1% w/v–10% w/v. The period of treatment with the lipase may be from about 5 min to approximately one hour, and at a temperature from at about 20° C. to approximately 37° C.

The nuclease may be in the concentration range of at about 0.1 units/ml to approximately 10 units/ml. The period of treatment with the nuclease may be from about 5 min to approximately one hour, and at a temperature from about 20° C. to approximately 37° C.

After each of the protease, lipase and nuclease steps, the vascular tissues are washed in pre-warmed phosphate-buffered saline (PBS) or water. The tissues are then treated with the following steps: a) detergent at a concentration of about 10%; b) dehydrocholic acid at a concentration of about 5% to approximately 30%; c) distilled water washes; and d) a solution of sodium dodecyl sulfate at a concentration from about 0.5% w/v to about 10% w/v. The detergent and subsequent steps may be performed at a temperature from about 20° C. to about 37° C. In this embodiment of the present invention the decellularized vascular tissue is stored in an alcohol solution.

Another preferred embodiment of the present invention is a method to immobilize an anti-thrombogenic agent to at least one surface of the decellularized vascular tissue by perfusing the tissue with a solution of hydroxylamine at a concentration from about 0.5 M to about 1.0 M, followed by perfusion with a solution of a linker molecule such as, but not limited to, 1-ethyl-3 (3-dimethylaminopropyl) carbodiimide (EDC) and an anti-thrombogenic agent such as, but not limited to, heparin, in a weight ratio of about 1:1.

In a most preferred embodiment of the method of the present invention, the decellularized and heparinized vascular prosthetic tissue is treated for approximately 5 min with a solution of a growth factor such as, but not limited to, bFGF at a concentration of about 5 μg/ml to about 50 μg/ml.

In other embodiments, the decellularized, heparinized, and growth factor-treated grafts can include other compounds with therapeutic properties including, but not limited to, urokinase, nitric oxide donors, gene delivery vectors, or other vasoactive drugs. These compounds can prevent graft thrombosis or modulate the graft healing process, regulate hemostasis or otherwise modify the physiology of the graft or of the graft recipient.

It should be understood, of course, that the foregoing relates only to preferred embodiments of the present invention and that numerous modifications or alterations may be made therein without departing from the spirit or the scope of the invention. The invention will be described in greater detail by way of specific examples. The following examples are offered for illustrative purposes, and are intended neither to limit nor define the invention in any manner.

EXAMPLE 1
Method for Decellularization of Vascular Tissue

The present invention included a procedure that could effectively remove all the cellular components of dissected vascular tissue while leaving the extracellular collagen and elastin framework intact. The preferred decellularization protocol follows.

Vascular tissue was immersed in distilled water for about 4 days at approximately 4° C. The distilled water was changed daily. The loosened adventitia tissue was cut from the vessels. Decellularized tissue was washed 3 times in 200 ml phosphate-buffered saline (PBS), pH 7.4, pre-warmed to 37° C. The vascular tissue was then sequentially soaked in: (i) 200 ml of 0.25% trypsin-EDTA, for 30 minutes at 37° C.; (ii) 3 times in PBS, pH 7.4, pre-warmed to 37° C., 200 ml per wash; (iii) 200 ml of 0.5% lipase, for 30 minutes at 37° C.; (iv) 3 times in PBS, pH 7.4, pre-warmed to 37° C., 200 ml per wash; (v) 3 times in PBS, pH 8.8, pre-warmed to 37° C., 200 ml per wash; (vi) 200 ml of micrococcal nuclease, 1 unit/ml, for 30 minutes at 37° C.; (vii) distilled water at 37° C.; (viii) 200 ml of Triton X-100, 10%, for 10 minutes at 37° C.; (ix) distilled water at 37° C.; (x) 200 ml of dehydrocholic acid, 10%, for 10 minutes at 37° C.; (xi) distilled water; (xii) SDS, 10%, 200 ml for 10 minutes at 37° C.; and (xiii) distilled water at 37° C. The decellularized tissues were sterilized and stored in 70% ethanol at 4° C., or frozen.

More than 200 vessels, including fresh pig carotid artery harvested from a local slaughterhouse and fresh dog external jugular vein (EJV) valves, were processed with this procedure.

EXAMPLE 2
Light Microscopic and Transmission Electron Microscopic (TEM) Examination Histological examination of pig carotid arteries after the decellularization process showed intact internal elastic lamina and elastin lamellar sheets in the media. Hematoxylin and eosin staining did not show any signs of remaining nuclear material in the vessel walls, indicating successful decellularization through the thickness of the vessels. TEM was performed to investigate microstructural changes in the vessels resulting from the decellularization and heparin immobilization processes, and to confirm removal of cellular debris. Results showed complete removal of cellular matter from the medial layers while the basic extracellular microstructure remained intact. Histological staining of a dog EJV valve before the decellularization process showed endothelial cells on the luminal surface of the vein and valve. Smooth muscle cells (SMCs) were present in the media of the vessel. In a decellularized dog EJV valve, on the other hand, all the endothelial and SMCs were removed, leaving the collagen and elastin extracellular matrix proteins. The valve retained its structural integrity.

EXAMPLE 3
Biotinylation of Decellularized Vascular Tissue

Biotinylation of decellularized grafts permitted a study of graft matrix protein metabolism and remodeling after implantation, since histological staining demonstrated the original graft matrix. Newly-formed decellularized prostheses were biotinylated by amino group substitution, using N-hydroxysuccinimidyl-biotin. The decellularized vascular tissues were immersed in 10 ml of N-hydroxysuccinimidyl-biotin (1 nmol/μl in N,N-dimethylformamide) or biotinamidocaproate N-hydroxysuccinimide ester (1 nmol/μl in N,N-dimethylformamide), and incubated on a shaker for 18–24 hours at room temperature. The grafts were then washed in distilled water and stored at 4° C. The efficiency of biotinylation was examined by streptavidin-peroxidase staining according to the method of Chen et al., J. Surg. Res. 60, 409–416 (1996), incorporated herein by reference in its entirety.

More than 50 decellularized arteries were biotinylated using the procedure described above. All the vessels showed strong streptavidin-peroxidase staining, indicating successful biotinylation. To test the stability of biotin labeling, biotinylated vessels were incubated in a tissue culture incubator. No signficant attenuation of biotin staining was found following 80 days of incubation.

EXAMPLE 4
Immobilization of Heparin and bFGF to Decellularized Vascular Tissue Decellularized vessels consist primarily of collagen and elastin matrix proteins that have low immunogenicity. These proteins are the most suitable substrates for vascular cell attachment, proliferation, migration, metabolism, and differentiation. Decellularized vessels, however, expose collagen, which has high thrombogenicity, on the luminal surface. Covalent immobilization of heparin to graft matrix proteins reduces the thrombogenicity of the prosthesis.

bFGF has a strong affinity for heparin ($K_d = 2 \times 10^{-9}$M). The heparinized grafts bound with bFGF offer enhanced endothelialization and transgraft cell migration, and an accelerated graft-healing process. Accelerated healing of biohybrid venous valve grafts with complete endothelialization, subendothelial tissue remodeling, and neoangiogenesis may improve long-term graft patency and preserve valve function. Detailed techniques are described below.

Heparin was immobilized by linkage to amino groups of the decellularized extracellular matrix proteins. A decellularized and biotinylated graft was perfused with hydroxylamine sulfate (1M). The graft was installed in a circulating system, and hydroxylamine sulfate salt was pumped through the vessel at a rate of 7.4 ml/min, for 1 hour. The crosslinking agent 1-ethyl-3(3-dimethylaminopropyl) carbodiimide (EDC) activated the carboxyl groups of heparin. Immobilization of heparin on pretreated grafts was carried out by circulating a heparin-EDC solution (1:2 weight ratio) through the circulation system at a rate of 7.4 ml/min for 18 hours at room temperature. A pH of 1.5 was maintained with 0.05M hydrochloric acid. After the reaction, distilled water was circulated through the graft at 7.4 ml/min for 1 hour to wash out unbound heparin. The graft may then be sterilized and stored in 70% ethanol at about 4° C. After storage in 70% ethanol, the heparinized grafts were rinsed in physiologicalal saline, and then immersed and soaked in 2 ml of bFGF (50 μg/ml) for 5 minutes, before immediately implanting in the recipient patient or animal.

EXAMPLE 5
Heparin Efficiency and Stability after Heparin Immobilization on the Vascular Tissues A colorimetric assay was used to determine the amount of heparin in a sample. In preparing a calibration curve, 2.5 ml of toluidine blue O was placed in each of seven test tubes. Various amounts of heparin, from about 0.01 to 0.07 mg, were added to the dye and the volume adjusted to 5 ml with 0.2% w/v sodium chloride. The test tubes were agitated for 30 seconds. N-hexane, 5 ml, was added to each tube and vortexed for 30 seconds. The aqueous layer was diluted 1:10 with ethanol, and the optical density of each sample was determined spectrophotometrically at 631 nm within 30 min of the reaction.

The heparinized graft was analyzed for heparin content by placing a 1 cm segment of a graft into a test tube, and adding 2.5 ml of toludine blue O, and 2.5 ml of 0.2% w/v sodium chloride. The procedure continued as for the soluble heparin assay described in the previous paragraph.

More than 200 decellularized arteries were covalently linked with heparin. Heparin assays were performed using a toludine blue O assay method as described above. The heparin binding efficiency was examined by quantification of heparin content immediately following the heparin immobilization procedures.

Paraffin sections of decellularized vessels with or without heparin treatment were stained with toludine blue (0.05% mg/ml concentration) to further examine the efficacy of the heparin immobilization process. Vessels with heparin treatment showed even positive staining with toludine blue through the entire thickness of the vessel walls, whereas decellularized vessels without heparin treatment did not stain with toludine blue. These results indicated that heparin was successfully linked to the decellularized vessels through their thickness.

Heparin binding stability was tested using the toludine blue colormetric assay after either storage of the heparin-bound graft in 70% alcohol or incubation in PBS at 37° C. for 1 day, 7 days, 14 days and 21 days respectively.

Minimal loss of heparin from heparinized pig or dog decellularized arteries was observed, even after 10 days at 37° C. These data demonstrate: (a) that the heparin immobilization procedure is effective and reliable, (b) biotinylation of the vascular prostheses prepared according to the present invention does not affect the heparin binding efficiency, and (c) heparin linkage is stable for at least 21 days. Furthermore, the processed grafts are easily sterilized with 70% alcohol and are stable during long-term storage. The heparin-linked prostheses did not lose significant amounts of heparin even after 2 years of storage in the 70% alcohol.

bFGF Binding

Figure 3A:
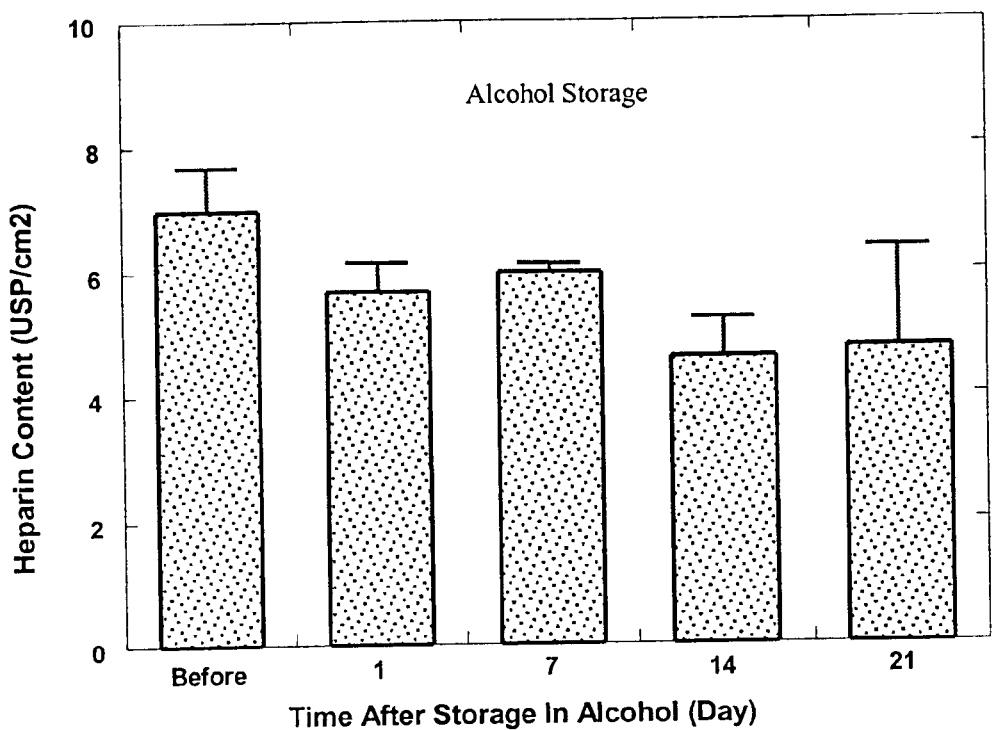
FIG. 3A shows the heparin covalent linking efficiency and stability of decellularized pig arteries when stored in 70% alcohol for various lengths of time.
Figure 3B:
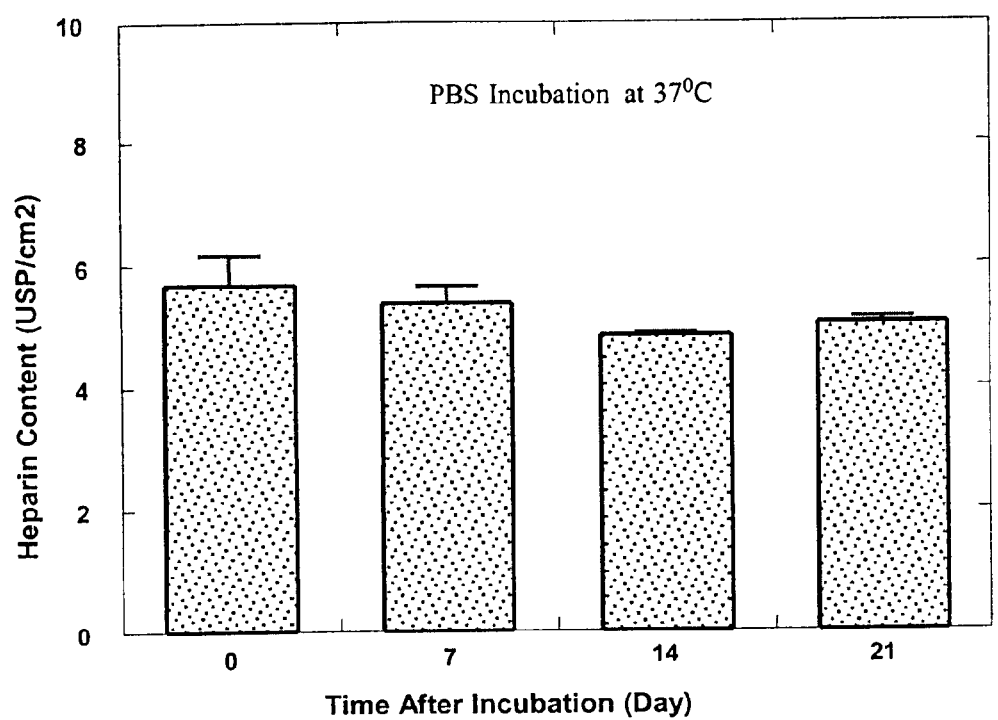
FIG. 3B shows the heparin covalent linking efficiency and stability of decellularized pig arteries when incubated in PBS at 37° C. for various lengths of time.

After storage in 70% ethanol, the heparinized grafts are rinsed in physiologicalal saline, and then immersed and soaked in 2 ml of bFGF (50 μg/ml) for 5 min, before immediately implanting in the recipient patient or animal. FIGS. 3A and 3B show the heparin covalent linkage of decellularized pig carotid arteries after storage in 70% alcohol for a different period of time and incubation in PBS at 37° C. for a different period of time.

EXAMPLE 6

Measurement of Blood Coagulation Induced by Vascular Grafts (Glass Test Tube Method)

Segments of vessels, with or without heparin treatment, 2 cm in length were incubated in PBS at 37° C. for 0, 3, 7, 14 or 21 days. After incubation, vessels were cut open longitudinally and a 1 cm² piece was cut from the middle of each vessel. The adventitia was gently removed from each sample by gentile dissection. Each square tissue sample was then cut into 9 equal size pieces and placed into 5 ml glass tubes.

Venous blood was drawn from the same human volunteer for each study and subsequently 2 ml of blood was quickly placed into each glass tube with the tissue samples. Tubes were then quickly covered with parafilm and placed in a sample rocker. The tubes were visually inspected for clots forming on the tissue samples as they rocked. The elapsed time between when the blood was applied to the sample and the formation was recorded as the clot time. Tests were stopped after one hour if no clot had formed. Three heparin treated vessels and two control vessels were tested at each time point. All control vessels formed clots with an average clot time of 13.9±minutes. None of the heparin treated vessels formed clots during the 60 minute duration of the test. These results indicate that the heparin remains effective in making the vessels non-thrombogenic despite its covalent linkage to the vessel wall. Further, the heparin linkage remained stable during 3 weeks of incubation in PBS at physiological temperatures. Table 1 depicts the results of the in vitro time assay.

TABLE 1

| | In vitro clot time assay | |
|---|---|---|
| Day | Heparin | Control |
| 0 | −(>60 min) | −(>60 min) |
| 3 | −(>60 min) | +(7.1 min) |
| 7 | −(>60 min) | +(12.1 min) |
| 14 | −(>60 min) | +(20.5 min) |
| 21 | −(>60 min) | +(19.4 min) |

Heparin treated decellularized graft segments (Heparin) did not form clots within the 60 minute duration of the test after incubation after up to 21 days in PBS at 37° C. whereas non heparin treated decellularized graft segments (Control) all formed clots.

EXAMPLE 7

Animal Implantation of Decellularized Non-heparinized Vascular Tissue

Pig arteries decellularized and heparinized by the methods described in Examples 1–5 have excellent handling characteristics, including good flexibility, ease of suture placement, and minimal needle-hole bleeding. Three decellularized and heparinized pig carotid arteries (xenografts) were implanted into the right carotid arteries of three dogs. Each dog received one graft. No anticoagulation was given to the dogs postoperatively. One dog and two dogs sacrificed at 24 and 67 days, respectively, had patent grafts. Anastomoses were completely healed without lumen dilation.

The graft that was patent at 24 days showed that fibroblast cells had invaded the decellularized graft matrix and non-continuous, endothelial-like cells covered the luminal surface. The grafts that were patent at 67 days had extensive luminal coverage with endothelial cells as shown by positive staining for the endothelial cell-specific Factor VIII-related antigen. Smooth muscle cells displaying α-actin immunoreactivity were present at both original matrix areas. These results show that the decellularized and heparinized graft surface was non-thrombogenic, and that patent grafts demonstrate accelerated healing and remodeling characteristics necessary to maintain long-term patency. Two additional dogs received bilateral femoral arteriovenous grafts (decellularized and heparinized pig cartotid arteries) for one month. Histological examination showed extensive host cell infiltration and accelerated healing process.

EXAMPLE 8

The Effect of Heparin on the Deposition of Platelets on a Decellularized Vascular Prosthesis, and the Function of Vascular Valve Prostheses The degree of baseline platelet deposition on a fresh dog EJV valve and a decellularized dog EJV valve, and the effect thereon of biotinylation, covalent linkage of heparin, and bFGF binding to heparin are studied. The combined effect of decellularization, biotinylation, and heparinization on venous valve function is examined in an ex vivo arteriovenous (A-V) shunt study. Detailed techniques are explained in the following paragraphs.

Platelet Radioactive Labeling and ex vivo A-V Shunt Platelet Deposition.

Autologous platelets are labeled with indium oxide. Approximately 30 min before the shunt study, the labeled platelets are intravenously reinfused into the animals. Six adult mongrel dogs are anesthetized with sodium thiamylal (15 mg/kg), and maintained on isoflurane. The carotid artery and EJV are isolated and cannulated to the respective entrance and exit ends of an A-V shunt. The A-V shunt consists of one segment each of the graft materials, connected in series. Grafts are nominally 6 mm in diameter and approximately 5 cm long. Blood flow is adjusted to approximately 100 ml/min by partially occluding the exit tubing of the shunt. Three graft images are taken at 30 min intervals.

Venous Valve Testing System

A venous valve testing system consists of a vessel adapter, two syringes, two pressure meters, and an angioscope system. Venous valve closure and opening are directly visualized on the screen and recorded on videotape. Pressures downstream and upstream of a valve are recorded simultaneously.

Five pairs of fresh and decellularized dog EJV valves are tested in this system and meet the criteria of a functional venous valve. Thus, a fully functional venous valve with an external support opens and closes completely at pressure gradients below 3 about, and after valve closure, no reflux occurs at pressures exceeding 100 about. At zero pressure valve leaflets are open. No differences are noted between fresh and decellularized venous valves.

EXAMPLE 9
Effects of bFGF on Cell Proliferation and Migration in vitro

Smooth muscle cells (SMCs) and endothelial cells were isolated from the dog carotid artery and femoral vein, respectively. For the cell proliferation assay, SMCs or endothelial cells were plated in 24-well plates, and variable amounts of bFGF were added to quadruplicate wells after 24 hours. Cells without added bFGF were used for control. Cells were counted according to the methods provided in Chen et al., J. Surg. Res. 69, 300–306 (1997), which is incorporated herein by reference in its entirety.

Figure 2A:
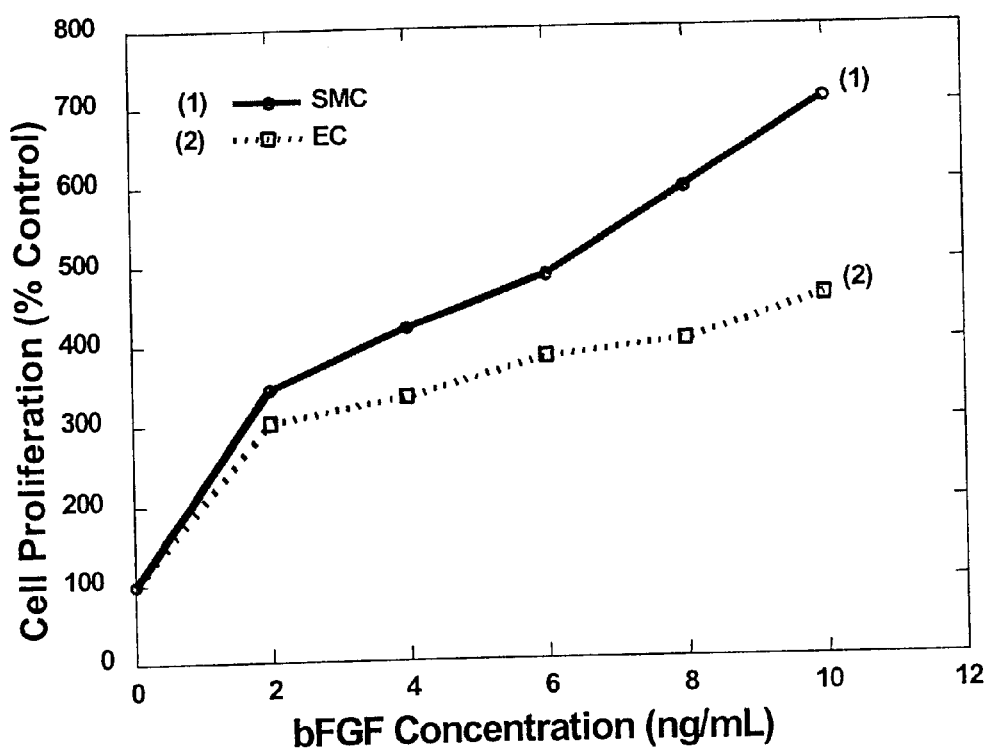
FIGS. 2A and 2B show the effect of bFGF on cell proliferation and migration in vitro.
Figure 2B:
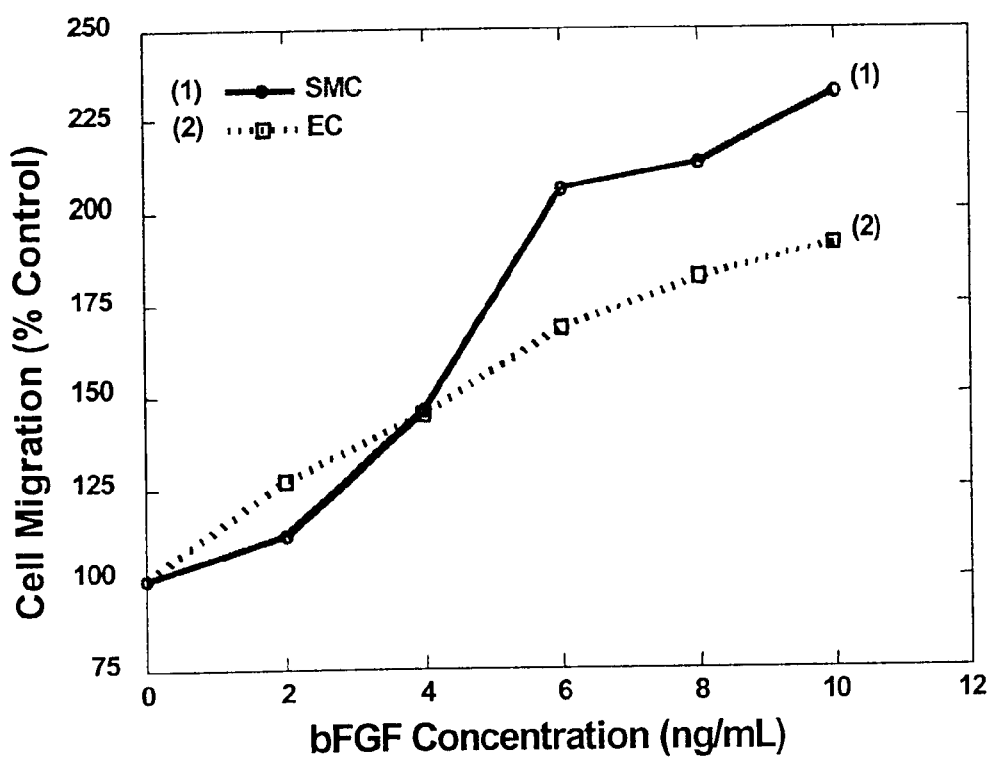

Cell migration was assayed in a modified Boyden chamber with a cellulose nitrate filter having 5 $\mu$m diameter pores. Cells and variable amounts of bFGF were added to the chamber. After incubation for 3 hours, cells that migrated through the pores were counted. The effects of bFGF on cell proliferation and migration are shown in FIGS. 2A and 2B, respectively. Human recombinant bFGF had a potent positive effect on canine smooth muscle cell and endothelial cell proliferation and migration. These results demonstrate the role of bFGF in accelerating vascular graft healing.

EXAMPLE 10
Venous Valve Allograft Performance

The performance of a biohybrid venous valve allograft is compared to an autogenous EJV valve in a paired study fashion. A biohybrid venous valve allograft is implanted into one dog femoral vein by end-to-end anastomosis. An autogenous EJV valve is likewise implanted into the opposite femoral vein. Dogs are assigned to 5 groups of 6 dogs per group. The groups are scheduled for sacrifice at 7 days, 14 days, 28 days, 3 months, and 6 months. Parameters that are evaluated include patency rate, valve function, morphometry, matrix remodeling, and the cellular composition of the graft wall (i.e. endothelial cells, SMCs, T cells, B cells, macrophages, and neutrophils).

Adult male mongrel dogs are anesthetized. Following the dissection of appropriate lengths of one EJV and both femoral veins, heparin (100 units/kg) is administered systemically and vascular control obtained. A 5 cm segment of EJV valve is removed and implanted into a femoral vein with a PTFE graft cuff. A biohybrid venous valve allograft is placed in the contralateral femoral vein. Contrast phlebography is performed immediately after graft implantation and at sacrifice. Angioscopic evaluation and pressure testing of each valve are also performed after harvest. All dogs are anticoagulated with Coumadin beginning 1 week before surgery using the technique of Rosenberg et al. (J. Neurochem. 46, 640–648 (1985)), which is incorporated herein by reference in its entirety. Bromodeoxyuridine administration, sacrifice, in situ perfusion fixation and specimen harvesting are performed as described by Chen et al. (Ann. Vasc. Surg. 10, 147–155 (1996); J. Vasc. Surg. 22, 237–247 (1995)), which are incorporated herein by reference in their entireties. Histological, morphometric, immunocytochemical, and statistical analysis are performed by techniques well known to one of ordinary skill in the art.

EXAMPLE 11
Decellularized, Heparinized and Growth-factor Coated Pig Arterial Grafts Pig carotid arteries, about 4 mm in diameter, are decellularized, leaving mainly collagen and elastin matrix proteins. Because the amino acid sequences of collagen and elastin are highly conserved across species, this matrix-based graft is less immunogenic when implanted in pigs (allogenic graft) or in other species (xenogenic graft). Unlike synthetic collagen tube grafts that do not contain elastin and are inflexible, the decellularized prostheses of the present invention maintain the native configurations of collagen and elastin and also their strength, elasticity and flexibility. There is reduced stretch pressure and hyperplasia at anastomoses because of matched compliance between the grafts and host vessels. Biotinylation of the decellularized grafts permits study of graft matrix protein metabolism and remodeling after implantation since the histological biotin-streptavidin-peroxidase staining technique traced the original graft matrix.

A decellularized pig artery has exposed, highly thrombogenic, collagen on the luminal surface. Covalent linkage of heparin to amino groups of graft matrix proteins reduces graft thrombogenicity. Procedures and conditions for the heparin covalent linkage are described in Example 4. These procedures are modified to achieve heparin binding of approximately 15 USP heparin/cm$^2$ of the decellularized graft.

A 70% solution of ethanol was used to sterilize the graft and stabilize the heparin linkage. The ethanol did not cause protein denaturation. bFGF was bound to the graft as described in Example 4.

bFGF Binding Assay bFGF binding efficiency is tested by radiolabeling bFGF. bFGF binding stability is tested in vivo using a vessel perfusion system for various time periods of incubation at 37° C. bFGF is labeled with $^{125}$I by the method of Bashkin et al (Biochem. 28, 1737–1743 (1989)), which is incorporated herein by reference in its entirety. bFGF (100 $\mu$g) is mixed for 2.5 hours, on ice, with $^{125}$I-labeled Bolton-Hunter reagent in 400 $\mu$l of 100 mM sodium phosphate buffer at pH 8.5. Excess Bolton-Hunter reagent is quenched by adding 3 ml of water containing 0.2 mg lysine and incubating for 45 min on ice. Next, 300 $\mu$l of 0.5% gelatin is added and the reaction vial is washed with 3.5 ml of gel filtration buffer (50 mM Tris-HCl, 0.05% gelatin, 1 mM dithiothreitol, and 0.3 M NaCl, pH 7.5). The combined sample is subjected to gel filtration on a Sephadex G-25 column equilibrated with the same buffer.

The $^{125}$I-bFGF binding efficiency is measured by incubating various dilutions of $^{125}$I-bFGF with heparinized grafts. All grafts are washed 3 times in PBS and cut into 0.5 cm long segments and the radioactivity levels measured with a gamma counter.

The stability of $^{125}$I-bFGF binding to the heparinized grafts is tested by pumping PBS through bFGF-coated grafts at 100 ml/min at 37° C. The radioactivity remaining on the graft is measured at 4 hours, 8 hours, 24 hours, 48 hours, 7 days and 14 days.

Processed pig arteries maintain their strength (bursting at a pressure of 5 atmospheres) and have excellent handling characteristics, including good flexibility, ease of suture placement, and minimal needle-hole bleeding.

EXAMPLE 12
Ex vivo A-V Shunt Platelet Deposition

Six adult pigs, each weighing 40 to 60 kg, are anesthetized with sodium thiamylal (15 mg/kg), and intubated and maintained on 1% isoflurane. A ventral mid-line incision is made in the neck and the carotid artery and external jugular vein isolated. The vessels are cannulated with the respective entrance and exit ends of an A-V shunt. The pigs are not administered anti-coagulants. The A-V shunt consists of one segment each of graft materials connected in series. Medical grade polyethylene tubing with an inner diameter of about 3.17 mm is used to connect the individual segments, and to form the entrance and exit ends of the shunt. Grafts are nominally 4 mm in diameter, and approximately 5 cm long.

Autologous platelets are labeled with $^{111}$indium oxide. Approximately 30 min before the shunt study, the labeled platelets are intravenously reinfused into the animals. Blood flow is adjusted to approximately 150 ml/min by partially occluding the exit tubing of the shunt. Graft images are taken at 30 min intervals over 90 min with a gamma camera.

EXAMPLE 13
Modified Allogenic Vessels are Non-immunogenic and Non-thrombogenic, have Accelerated Healing, and Long-term Patency with Few Graft-related Complications The bioengineered small-caliber grafts from pig carotid arteries (allogenic) are implanted into the pig femoral arteries by end-to-side anastomosis. End-to-side anastomosis is the most commonly used method for small-caliber graft bypass in human arterial reconstruction procedures.
Group 1 (Heparin Effect)

The performance of a biotin-heparin-linked decellularized graft is compared to a biotin-linked graft. In each animal, one femoral artery receives a biotin-heparin-linked decellularized graft, and the contralateral vessel receives a biotin-inked decellularized graft as the internal control. Six pigs are used at each of 4 time points, at 1 week, 2 weeks, 4 weeks, and 3 months.
Group 2 (bFGF Effect)

To test whether bFGF accelerates graft healing, six pigs are assigned to each of 4 time points, at 1 week, 2 weeks, 4 weeks, and 3 months. In each animal, one femoral artery receives a biotin-heparin-linked decellularized graft with bFGF treatment, and the contralateral vessel receives a biotin-heparin-linked decellularized graft without bFGF treatment as an internal control.

Graft patency, blood cell count and coagulation parameters are regularly monitored. The cell responses are quantified, including graft endothelization, inflammatory infiltration by neutrophils, lymphocytes, and macrophages, and migration of fibroblasts and SMCs into the media of the graft. Graft material protein metabolism, mainly protein degradation, and absorption are documented. Morphometric measurements were recorded, including lumen diameters, neointimal thickness and area, and cell proliferation, at the anastomosis and mid-graft. Detailed protocols are listed below.

Adult male pigs weighing 40 to 60 kg are anesthetized. Following the dissection of appropriate lengths of femoral arteries, heparin (100 units/kg) is administered systemically and vascular control obtained. A decellularized graft, 5 cm in length with an inner diameter of 4 mm, is inserted into a femoral artery by end-to-side anastomosis, while a control graft (4 mm diameter, 5 cm long) is placed in a contralateral vessel. Pigs are sacrificed at 1 week, 2 weeks, 4 weeks, and 3 months. Graft patency is monitored by Doppler ultrasound. Blood is removed once a week to check the blood cell count and activated partial thromboplastin time (aPTT).

Bromodeoxyuridine (BrdU), 50 mg/kg dissolved in 50 ml of normal saline, is administered intraperitoneally 24 hours before sacrifice. At sacrifice, the animals are anesthetized, and the femoral arteries and grafts are exposed. Patency of grafts is determined by direct inspection, by blood flow measurement using an ultrasonic flowmeter, and by histological analysis.

A sternotomy is performed, and Ringer's solution infused at 120 about pressure through a wide-bore needle into the left ventricle while the animal is synchronously exsanguinated via a cannula placed in the right atrium. Once blood is cleared from the circulatory system, the animal is perfusion fixed in situ for 20 minutes at 120 about pressure using 2.5% glutaraldehyde in PBS. Grafts with 3 cm segments of attached femoral artery are harvested, fixed in 10% buffered formalin overnight and transferred to 70% alcohol.

Cross sections of specimens are taken perpendicular to the long axis of the vessel, at a distance of 2 mm between the heel and toe of each anastomosis, and at 5 mm intervals along the entire graft length and attached native vessels. The specimens are embedded in paraffin and sections are cut and stained with hematoxylin and eosin, and Verhoeff-Masson's stain. Morphometric measurements of the thickness and area of neointima and luminal diameters are performed with a computer.

An avidin-biotin complex immunoperoxidase procedure was used to identify determinants characterizing cell types and proliferating cells by techniques well known to one skilled in the art. Primary monoclonal antibodies specific for α-actin, Factor VIII-related antigen, T-cell (CD43), B-cell (L26), and macrophage (HAM56), are used to identify smooth muscle cells, endothelial cells, T lymphocytes, B lymphocytes, and macrophages, respectively. For negative controls, pre-immune mouse serum is used instead of the primary antibody.

Proliferating cells are identified with anti-BrdU monoclonal primary antibody. BrdU-positive cells are quantified manually. Positively stained cells are expressed as a percentage of total cells, giving the BrdU index. At least 10 microscope fields are quantified per section.

Chi-square analysis is used to determine significance of differences in patency rates between the treated grafts and the control grafts. The paired Student's t test is used to compare the data of cell numbers and morphometric measurements. Results are considered significant if the p value was less than 0.05.

In all cases, the grafts of the present invention show superior patency, greater invasion of the graft by the host cells, and more extensive adsorption of the graft extracellular matrix protein, than is seen with any other type of glutaraldehyde-fixed biological graft with which the prostheses of the present invention are compared.

EXAMPLE 14
Comparison Between Bioengineered Allogenic Grafts of the Present Invention and Autogenous Vein Grafts and ePTFE Grafts, in the Pig Model This study compares bioengineered allogenic grafts of the present invention with autogenous vein grafts and ePTFE grafts, in the pig model. Pig saphenous vein is very short and narrower than the pig femoral artery and, therefore, is unsuitable as a femoral bypass graft. The pig epigastric vein, however, is long and has a similar diameter to that of the pig femoral artery.
Group 3 (Allograft vs. Autograft)

To compare bioengineered allografts of the present invention with fresh autogenous vein grafts, a biotinylated and heparin-linked allograft, with or without bFGF attached, is implanted into a pig femoral artery. A fresh autogenous epigastric vein graft is implanted into the contralateral vessel. Six animals are studied at 1 month and at 6 months.
Group 4 (Allograft vs. ePTFE Graft)

To compare bioengineered allografts of the present invention with ePTFE grafts, a biotinylated and heparin-linked allograft, or the same graft with bFGF also attached, is implanted into one pig femoral artery, and an ePTFE graft is implanted into the contralateral vessel. Six animals are studied at 1 month and at 6 months.

The host cell incorporation, graft material protein degradation, and morphometric measurements are quantified. Graft patency, blood cell count and coagulation parameters are regularly monitored. Detailed protocols are given in the preceding Examples.

In all cases, the grafts of the present invention show superior patency, greater invasion of the graft by the host cells, and more extensive adsorption of the graft extracellular matrix protein, than was seen with PTFE grafts with which the prostheses of the present invention are compared.

EXAMPLE 15
Comparison Between Bioengineered Pig Xenogenic Prostheses of the Present Invention, and Autogenous Vein Grafts from Dog and ePTFE Grafts, in the Dog Model Cross-linked xenogenic biological vascular grafts have been used as an alternative choice of prosthesis in arterial reconstructions for many years. A major advantage of xenogenic grafts is their convenient supply in variable sizes as compared to allogenic grafts. Decellularized xenogenic grafts are less immunogenic, with better healing characteristics. Heparin covalent linkage prevents thrombosis, and bFGF treatment accelerates the vascular healing process and prevents graft degeneration. In this study, pig xenogenic grafts, bioengineered according to the present invention, are compared with autogenous vein grafts and ePTFE grafts in the dog model. The dog saphenous vein is relatively long and has a size similar to dog femoral artery. Therefore, the dog saphenous vein is used for the femoral bypass graft.
Group 5 (Xenograft vs. Autograft)

To compare bioengineered xenografts with fresh autogenous vein graft, a biotinylated and heparin-linked xenograft, or the same graft with bFGF attached, is implanted into a dog femoral artery, and a fresh autogenous saphenous vein graft is implanted into the contralateral vessel. Vessels are studied at 1 month and at 6 months. Six animals are sampled at each time point.

Group 6 (Xenograft vs. ePTFE Graft)

To compare bioengineered xenografts according to the present invention with ePTFE grafts, a biotinylated and heparin-linked xenograft, or a similar graft with bFGF attached, is implanted into one dog femoral artery, and an ePTFE graft is implanted into the contralateral vessel. Six animals are studied at 1 month and 6 months. The host cell infiltration, graft material protein degradation, and morphometric measurements are quantified. Graft patency, blood cell count and coagulation parameters are regularly monitored. Detailed protocols are given in the preceding Examples.

In all cases, the grafts of the present invention show superior patency, greater invasion of the graft by the host cells, and more extensive adsorption of the graft extracellular matrix protein, than was seen with any other type of graft with which the prostheses of the present invention were compared.

EXAMPLE 16
Histology of the Dog External Jugular Vein Valve

Cellular components were clearly seen in a normal dog external jugular vein valve. With decellularized dog external jugular vein valves, however, cellular components were completely removed.

EXAMPLE 17
Histology of the Dog EJV Valve

A normal dog EJV valve stained with hematoxylin and eosin showed endothelial cells. Decellularized dog EJV valves showed venous valves without endothelial cells.

EXAMPLE 18
Heparin Immobilization on Decellularized Biological Vascular Prostheses The decellularized grafts were everted (inside-out) and pre-treated with 1M hydroxylamine sulfate for 1 hour. The carboxyl groups of heparin were activated by the cross-linking agent 1-ethyl-3(3-dimethylaminopropyl) carbodiimide (EDC). Immobilization of heparin on decellularized grafts was achieved by incubating the decellularized vascular material overnight at 27° C. with heparin-EDC solution, 1:2 weight ratio, with the pH maintained at 1.5 with 0.05M hydrochloric acid. Unbound heparin was washed out by distilled water. A colorimetric assay was used to determine the amount of heparin in a sample as detailed in Example 5. The results are shown in the following Table 2.

|  | Heparin immobilization | |
|---|---|---|
|  | 1 day (USP/cm$^2$) | 10 days (USP/cm$^2$) |
| Pig carotid artery | 17.02 | 15.01 |
| Dog carotid artery | 14.71 | 13.62 |
| Dog external jugular vein | 13.33 | 12.07 |

EXAMPLE 19
Vascular Implantation into Dogs

Pig carotid arteries, prepared according to the present invention are implanted in the carotid artery and femoral artery and vein in dogs. Each dog receives bilateral carotid arterio-arterial bypass grafts and bilateral femoral arteriovenous grafts for periods of 1 week, 2 weeks, 1 month, 2 months, 3 months, and 6 months. The patency rate is documented with a weekly duplex ultrasound examination, as well as flow measurement at sacrifice. Vascular healing of the graft is analyzed with histochemical and immunohistochemical studies, including cell type identification, cell proliferation, morphometric analysis (luminal diameter, and neointimal thickness and area). Matrix protein metabolism is measured by biotin-streptavidin staining as described above in Example 3. The immune responses of the recipient dogs to the xenograft implantations are also studied, including complement system activation, specific antibody production to the pig collagen, and T cell specific activation to the pig collagen.

The role of bFGF binding in accelerating vascular healing is studied using paired internal controls in separate dogs. Six dogs are used in this study. Each dog receives a bFGF-bound graft in one carotid artery and another in one femoral artery and vein. Each dog also receives grafts, but without any bound bFGF on the contralateral side, in the carotid artery and femoral vein, as internal controls. The dogs are sacrificed at 1 month. Patency rate and vascular healing of the bFGF-coated and uncoated vascular prostheses are compared.

The in vivo performance of pig carotid artery grafts bioengineered according to the present invention is compared with autogenous saphenous vein grafts in the dog models, by both carotid arterio-arterial bypass grafts and femoral arterio-venous grafts. Six dogs are used in this study. Each dog receives one bioengineered xenograft in both the carotid artery and femoral vein, and the contralateral side received autogenous saphenous vein grafts as internal controls. Autogenous greater saphenous veins are harvested from the dogs' legs. The dogs are sacrificed at 1 month. Patency rate and vascular healing are compared between bioengineered xenograft and autogenous saphenous vein grafts.

The in vivo performance of the xenografts is compared with small caliber (with an inner diameter of 4 mm) ePTFE grafts. Six dogs are used in this study. Each dog receives one bioengineered xenograft at both carotid artery and femoral vein positions, and the contralateral sides receive ePTFE grafts as internal controls. The dogs are sacrificed at 1 month. Patency rate and vascular healing are compared between the xenografts and ePTFE grafts.

The in vivo performance of xenografts is compared with commercially available glutaraldehyde-fixed bovine carotid artery grafts (obtained from St. Jude Medical, Inc., St. Paul, Min.). Again, six dogs are used in this study. Each dog receives one bioengineered xenograft at both carotid and femoral positions, and the contralateral side receives glutaraldehyde-fixed bovine carotid artery grafts as internal controls. The dogs are sacrificed at 1 month. Patency rate and vascular healing are compared between the xenograft and the glutaraldehyde-fixed bovine carotid artery grafts.

Unmodified xenografts are compared to xenografts bioengineered according to the present invention. Six dogs are used for this study. Each dog receives one bioengineered xenograft in both the carotid artery and femoral vein and the contralateral side receives fresh pig carotid arteries as internal controls. The dogs are sacrificed at 1 month. Patency rate and vascular healing are compared between bioengineered xenograft and fresh pig carotid arteries.

Long term vascular remodeling and vascular functions are studied in the dog models of carotid arterio-arterial bypass grafts and femoral arterio-venous grafts. Three animals are used in this study. Each animal receives four bioengineered pig carotid arteries, two at the carotid position and two at the femoral position. Graft patency is determined every month by duplex ultrasound examination. Every three months starting from 6 months, vessel motor functions of vascular grafts are studied in response to norepinephrine for contraction, and to acetylcholine for endothelial dependent relaxation. Angiogram and graft luminal diameter analyses are performed in response to the vasoactive drugs. Alternative measurements of intraluminal vascular ultrasound (IVUS) for graft diameter changes in response to the drugs are performed. Animals are sacrificed at 3 years. The graft is harvested for myographic analysis of vessel motor functions and for histological and molecular analysis of normal smooth muscle cell, and endothelial cell phenotypes, as well as matrix components and structure.

EXAMPLE 20
Compliance Testing of Bioengineered Vascular Tissues

The compliance of vessels was determined using a custom built system. The system consisted of a digital pressure gauge (Cole-Parmer, Vernon Hills, Ill.), syringe pump (Harvard Apparatus, Holliston, Mass.), custom built adjustable cannula, tubing (Cole-Parmer), a video camcorder (Panasonic, Japan), and a Pentium II personal computer (Dell, Round Rock, Tex.) with a video acquisition board (Data Translations, Marlboro, Mass.). Vessels were sutured onto the adjustable cannula using 2-0 silk suture. Subsequently, the system was flushed with 37° C. PBS to remove air from the vessel segment and tubing. In order to reduce the effects of viscoelasticity, vessels were preconditioned with prior compliance testing by slow inflation to 220 mm Hg using the syringe pump followed by holding this pressure for 45 seconds. Next, vessels were slowly deflated to 0 mm Hg. After 4 inflation-deflation cycles to 220 mm Hg, vessels were inflated slowly to 200 mm Hg and the length of the cannula was adjusted to eliminate curvature in the vessel. The cannulas were then fixed at this length.

During compliance testing, the vessel and cannula assembly were submerged in a bath of PBS at 37° C. to simulate physiologicalal temperature conditions. After equilibration, vessels were inflated from 0 to 200 mm Hg in 10 mm Hg increments using the syringe pump. Subsequently, the vessels were deflated in 10 mm Hg increments. The outside diameters of the vessels were recorded at each pressure increment using the video camcorder. The video images were then downloaded onto a PC for diameter measurements. Vessel diameters were measured in pixels using Scion Image (Scion Corp., Frederick, Md.) for each of the pressure increments from 0 to 200 mm Hg and back to 0 mm Hg. The percent diameter change relative to the diameter at 0 mm Hg was calculated as $\Delta D=100\times(D_p-D_0)/D_0$, where $\Delta D$ is the percent diameter change, $D_p$ is the diameter at a specified pressure, and $D_0$ is the reference diameter at 0 mm Hg. Average compliance in the physiological pressure range, taken to be 70–130 mm Hg, was calculated as the slope of the linear regression line through the $\Delta D$ vs. pressure data between 70 and 130 mm Hg, and was expressed as percent diameter change per mm Hg change in pressure. The data were then normalized to the compliance of the fresh vessels, which was taken to be 100%.

The compliance was determined for decellularized and decellularized heparin treated vessels and compared to the compliance of fresh porcine common carotid arteries, alcohol preserved porcine common carotid arteries, ePTFE vascular grafts, and commercially-available glutaraldehyde fixed bovine carotid artery and human umbilical vein (HUV) vascular grafts. The ePTFE grafts (n=2) were the stiffest, changing in diameter by only 2.8% over the range of 0–200 mm Hg (FIGS. 1A, and B). The Glutaraldehyde-fixed bovine graft (n=2) was nearly as stiff as the ePTFE graft, only changing in diameter 4.8% over the range of 0–200 mm Hg, while the Glutaraldehyde-fixed HUV graft (n=2) only changed about 13.8% in diameter over the same range of pressure. Fresh, living vessels (n=4) increased in diameter by 73% over the 200 mm Hg pressure range, while decellularized vessels (n=4) were the least stiff, increasing by 88% in diameter between 0 and 200 mm Hg. The heparin immobilization process slightly stiffened the decellularized vessels (n=2), which increased in diameter by 69% over the range of the test, which was nearly identical to the behavior of the fresh vessels. Alcohol preservation of fresh vessels (n=4) stiffened them considerably relative to fresh live vessels as they only expanded in diameter by 56% over 200 mm Hg.

Figure 1B:
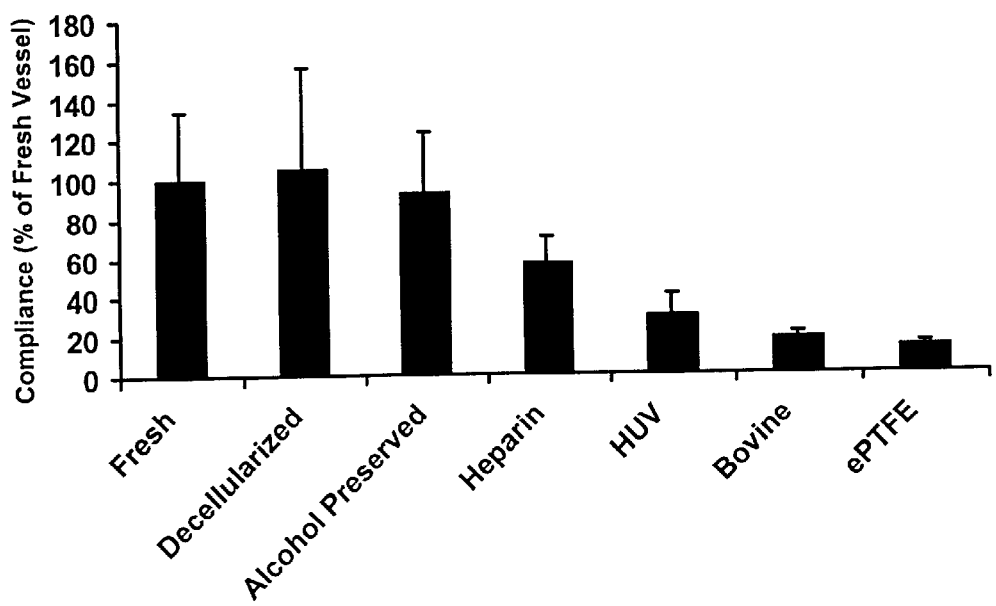

The average compliance of vessels in the physiological pressure range of 70–130 mm Hg was also calculated from the pressure-diameter data (FIG. 1B). The average compliance of fresh vessels during the inflation phase was 0.172%/mm Hg. Linkage of heparin to vessels further reduced the compliance in the physiological pressure range to 0.0975%/mm Hg, which was approximately 57% the compliance of the fresh vessels. For comparison, the compliance in the physiological pressure range of commercially available glutaraldehyde-fixed bovine artery and human umbilical vein as well as ePTFE grafts were also calculated. Glutaraldehyde-fixed HUV grafts only had a compliance of 0.053%/mm Hg, which was only 31% the compliance of fresh vessels. The compliance of Glutaraldehyde-fixed bovine artery grafts was 0.031%/mm Hg, which was only 18% of the compliance of fresh porcine common carotid arteries,. The least complaint samples tested were the ePTFE grafts, which had a compliance of only 0.024%/mm Hg, or about 14% of the compliance of the fresh vessels in the physiological pressure range. These results indicate that although the heparin treated decellularized vascular xenografts are less compliant than fresh native vessels in the physiological range, they are almost two fold as compliant as existing small caliber biologic vascular grafts and about four fold more compliant than synthetic grafts.

FIGS. 1A, and B show the pressure vs. diameter results for fresh porcine common carotid arteries (PCA, Fresh), alcohol preserved PCA (Alcohol Preserved), decellularized PCA, heparin treated decellularized PCA (Heparin), ePTFE graft, gluteraldehyde fixed human umbilical vein (HUV), and gluteraldehyde fixed bovine arteries (Bovine). Based on the pressure/diameter data, the average compliance in the physiological pressure range of 70–130 mm Hg was determined and compared to the compliance of fresh vessels. Decellularized vessels were the most compliant, followed by fresh vessels, alcohol preserved, and heparin treated vessels, respectively.

EXAMPLE 21

Burst Strength Testing of Bioengineered Vascular Tissues

The apparatus used in burst testing vessels was the same used in the compliance tests. Vessels were sutured to the cannula using 2-0 silk sutures and allowed to lengthen freely as pressure was increased. Vessels were inflated with PBS at room temperature at the rate of approximately 45 mm Hg/second while the inflation pressure was recorded from the pressure gauge on a Pentium II personal computer (Gateway, North Sioux City, S.Dak.) with a data acquisition board (National Instruments Co., Austin, Tex.). The burst pressure was defined as the highest pressure reached before failure of the vessel up to the 2300 mm Hg limit of the pressure transducer.

Figure 4:
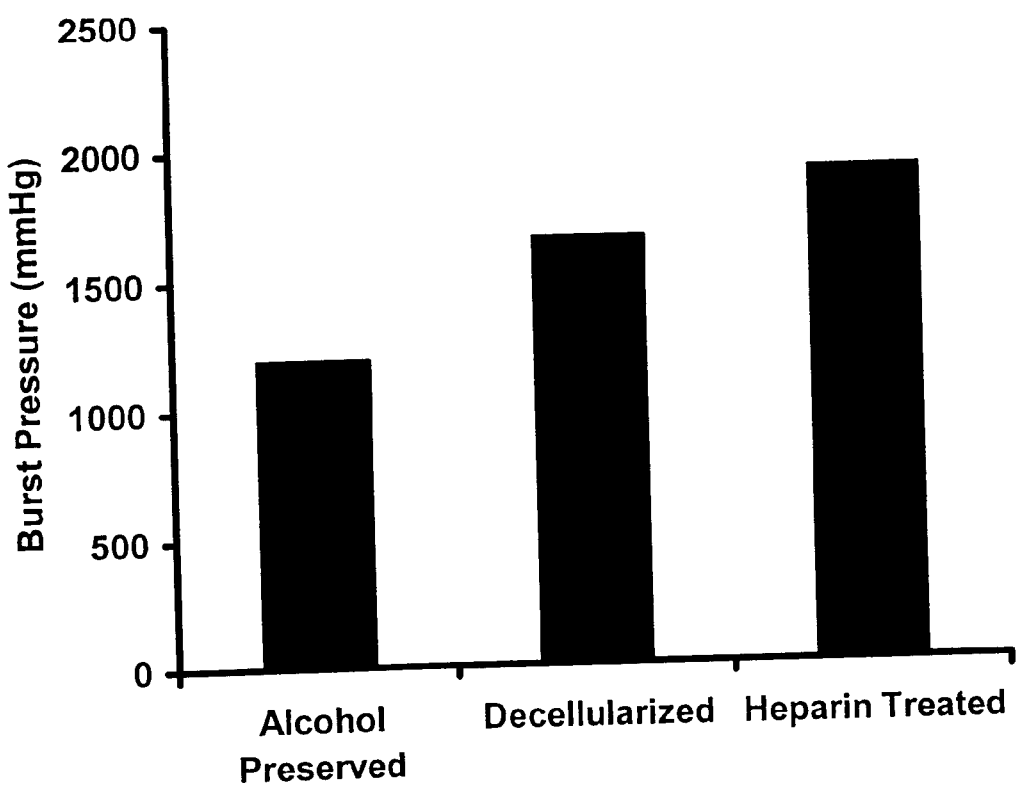
FIG. 4 shows the burst pressure of vessels which have been preserved in alcohol, decellularized or treated with heparin.

Of the fresh vessels tested (n=4), none burst within the 2300 mm Hg limit of the test. One out of four alcohol preserved vessels burst at a pressure of 1194 mm Hg, as did one out of four decellularized vessels at 1654 mm Hg (FIG. 4). Two heparin treated vessels were tested and one burst at 1912 mm Hg while the other did not up to the pressure limit of the test. These results indicate that although some of the strength of the vessels may be lost during processing, they still have a high safety margin of over 10 times physiological pressure.

FIG. 4 shows the results when the vessels were tested to determine the maximum pressure they could withstand before bursting in order to assure safety after implantation. None of the four fresh vessels burst up to the test limit of 2300 mm Hg pressure. Out of four alcohol preserved and decellularized vessels tested, only one of each burst up to the pressure limit of the test. Two heparin treated vessels were tested and one burst. These results indicate the heparin treated graft is sufficiently strong to withstand physiological pressures.

EXAMPLE 22

Suture Retention Strength Testing of Bioengineered Vascular Tissues

A custom apparatus was used in testing vessels for suture retention strength consisting of a force transducer (Omega Engineering Inc., Stamford, Conn.), digital meter (Omega), data acquisition board (National Instruments), Pentium II personal computer (Gateway), and a motorized stage (Harvard Apparatus). Sections of vessels 3–4 cm in length were cut at a 45° angle at one end and the other end was clamped in the stage clamp of the suture retention device. A suture was then placed in the angled end of the vessel at the toe, heel, left, or right side, 2 mm from the end, looped through a hook on force transducer, and the ends of the suture were tied together with a minimum of 7 knots to prevent slippage. The vessel was then pulled away from the force transducer at a constant rate of 0.8 mm/second until the suture pulled out of the vessel or the suture broke. The maximum force on the suture was recorded as the suture retention strength of the vessel.

Figure 5A:
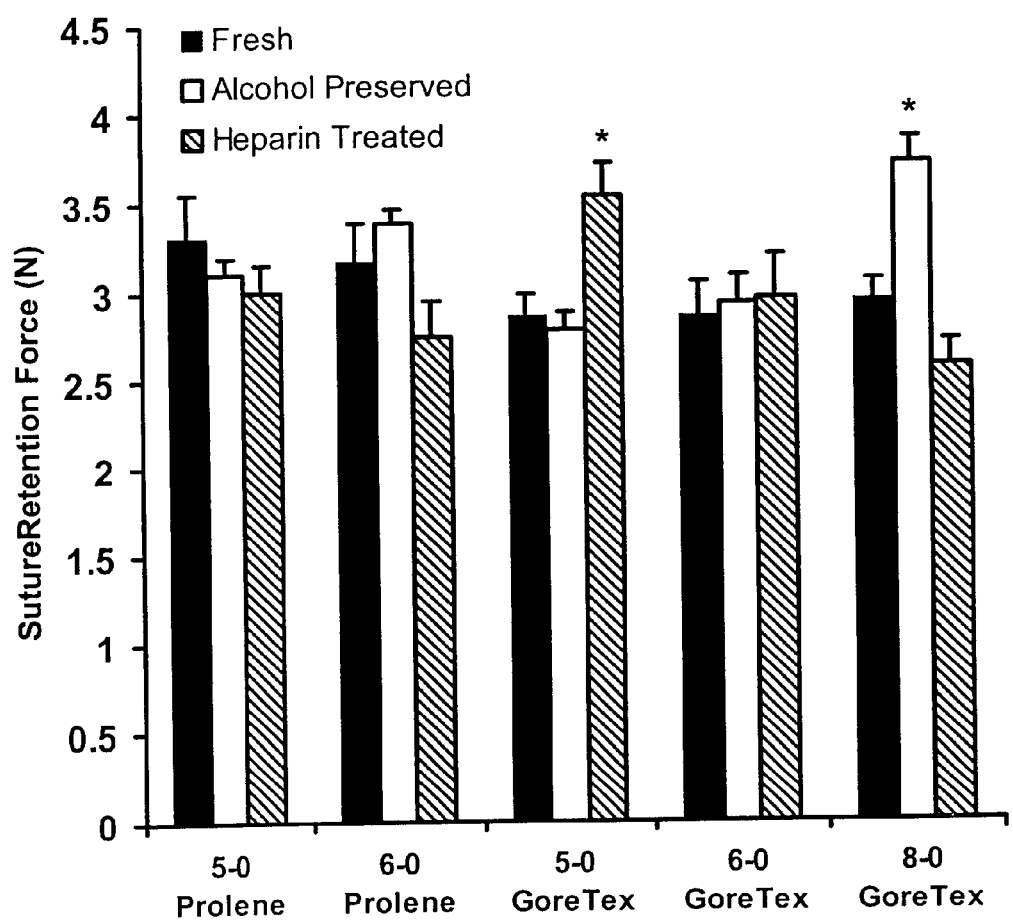
FIGS. 5A and 5B show the suture retention of fresh, alcohol preserved and heparin treated vessels.
Figure 5B:
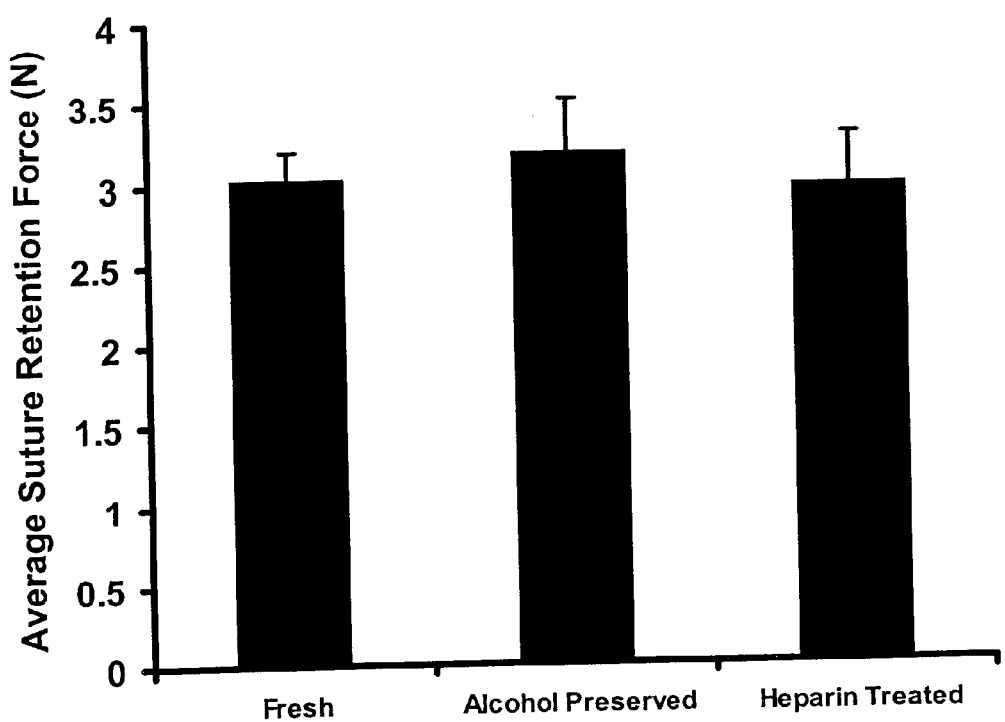

Five types of sutures commonly used in vascular anastomosis construction were used. Each type of suture was tested three times in the heel, toe, left and right positions of fresh, alcohol preserved, and heparin treated vessels. The average of the resulting 12 tests for each suture-vessel combination were compared (FIG. 5A). Heparin treated vessels had a significantly higher (P<0.05) suture retention strength with 5-0 GoreTex suture compared to fresh and alcohol preserved vessels, while alcohol preserved vessels had a significantly higher, suture retention strength with 8-0 GoreTex relative to fresh and heparin treated vessels. There was no difference in the average suture retention strength for all types of sutures tested between fresh, alcohol preserved, and heparin treated vessels (FIG. 5B). Thus heparin treated grafts should have enough suture retention strength to withstand in vivo anastomotic forces.

FIGS. 5A and B show suture retention strength determined for fresh, alcohol preserved, and heparin treated vessels using 5 clinically relevant sutures (A). Heparin treated vessels had significantly higher suture retention strength with 5-0 GoreTex suture, while alcohol preserved vessels had significantly higher suture retention strength with 8-0 GoreTex suture. The average suture retention strength for each type of vessel was found by averaging the strengths for the 5 types of sutures used (B). There was no significant difference between fresh, alcohol preserved, and heparin treated vessels.

The disclosures of all publications cited in this application are hereby incorporated by reference in their entireties.

The present invention has been illustrated in great detail by the above specific Examples. It is to be understood that these Examples are illustrative embodiments and that this invention is not to be limited by any of the Examples or details in the Description. Those skilled in the art will recognize that the present invention is capable of many modifications and variations without departing from the scope of the invention. Accordingly, the Detailed Description and Examples are meant to be illustrative and are not meant to limit in any manner the scope of the invention as set forth in the following claims. Rather, the claims appended hereto are to be construed broadly within the scope and spirit of the invention.

What is claimed is:

1. A vascular prosthesis comprising a decellurized vascular tissue linked covalently to an anti-thrombogenic compound, said anti-thrombogenic compound being further linked to a growth factor.

2. The vascular prosthesis of claim 1, wherein the decellularized vascular tissue is a blood vessel, a valve dissected from a blood vessel, a valve retained within a portion of blood vessel, an aortic value or a pulmonary valve.

3. The vascular prosthesis of claim 1, wherein the anti-thrombogenic compound is a glycosoaminoglycan.

4. The vascular prosthesis of claim 3, wherein the glycosoaminoglycan is heparin.

5. The vascular prosthesis of claim 4, wherein the growth factor has a high affinity to heparin.

6. The vascular prosthesis of claim 4, wherein the growth factor is linked to the decellularized vascular tissue by means of attachment to the heparin.

7. The vascular prosthesis of claim 1, wherein the anti-thrombogenic compound is dextran, hirudin, coumarin, thrombolytic agents, derivatives thereof or a combination thereof.

8. The vascular prosthesis of claim 1, wherein the growth factor is fibroblast growth factor, basic fibroblast growth factor, acidic fibroblast growth factor, heparin-binding epidermal growth factor, transforming growth factor alpha, transforming growth factor beta, vascular endothelial cell growth factor, placenta growth factor, insulin-like growth factor or a combination thereof.

9. The vascular prosthesis of claim 1, wherein the growth factor promotes growth of endothelial and smooth muscle cells.

10. The vascular prosthesis of claim 1 further comprising a pharmaceutically active agent.

11. The vascular prosthesis of claim 10, wherein the pharmaceutically active agent is a thrombolytic agent, a nitric oxide donor, a gene delivery vector or a vasoactive drug.

12. The vascular prosthesis of claim 11, wherein the thrombolytic agent is plasmin, plasminogen, urokinase or thrombin.

13. The vascular prosthesis of claim 11, wherein the vasoactive drug regulates growth of vascular tissues or regulates vascular tone.

14. The vascular prosthesis of claim 1 further comprising a stent.

15. The vascular prosthesis of claim 1, wherein the vascular prosthesis is immunologically acceptable to a recipient.

* * * * *